(12) United States Patent
Wolf et al.

(10) Patent No.: US 7,919,673 B2
(45) Date of Patent: Apr. 5, 2011

(54) TRANSGENIC PIG WITH ALTERED INCRETIN FUNCTION

(75) Inventors: Eckhard Wolf, Vierkirchen (DE); Simone Renner, München (DE); Barbara Kessler, München (DE); Rüdiger Wanke, München (DE); Nadja Herbach, München (DE); Alexander Pfeifer, Bonn (DE); Andreas Hofmann, Bonn (DE)

(73) Assignees: Ludwig-Maximilians-Universitat, Munich (DE); MWM Biomodels GmbH, Tiefenbach (DE)

( * ) Notice: Subject to any disclaimer, the term of this patent is extended or adjusted under 35 U.S.C. 154(b) by 0 days.

(21) Appl. No.: 12/348,294

(22) Filed: Jan. 4, 2009

(65) Prior Publication Data
US 2009/0228993 A1 Sep. 10, 2009

Related U.S. Application Data

(60) Provisional application No. 61/019,001, filed on Jan. 4, 2008.

(30) Foreign Application Priority Data

Jan. 4, 2008 (EP) .................................. 08000111

(51) Int. Cl.
*A01K 67/027* (2006.01)
*A01K 67/00* (2006.01)
*A01K 67/033* (2006.01)

(52) U.S. Cl. .............................. 800/17; 800/14; 800/9
(58) Field of Classification Search ............... 800/17, 800/4
See application file for complete search history.

(56) References Cited

FOREIGN PATENT DOCUMENTS
EP 0 979 872 2/2000

OTHER PUBLICATIONS

Herbach et al, 2005, Regulatory Peptides, 125:103-117.*
Hofmann et al. EMBO reports, 2003, 4:1054-1060.*
Gerrity, Diabetes, 2001, 50:1654-1665.*
Renner, S. et al., "Glucose intolerance and reduction of pancreatic b-cell mass in transgenic pigs expressing a dominant-negative GIP receptor(GIPRdn) in the pancreatic islets," *Swine in Biomedical Research Conference Proceedings*, Apr. 2, 2008, p. 55, XP-002518911.
Renner, S. et al., "Impaired incretin effect in transgenic pigs expressing a dominant negative receptor for glucose-dependent insulinotropic polypeptide (GIP)," *National Genome Research Network*. Nov. 2007, Abstract.

* cited by examiner

*Primary Examiner* — Valarie Bertoglio
(74) *Attorney, Agent, or Firm* — Saliwanchik, Lloyd & Eisenschenk

(57) ABSTRACT

The present invention relates to transgenic pigs containing a dominant-negative incretin hormone receptor, namely the dominant-negative human glucose-dependent insulinotropic polypeptide receptor. The present invention furthermore relates to uses of these transgenic pigs as clinically relevant animal model systems for studying the pathogenesis and novel therapies for diabetes mellitus type 2, particularly for the maintenance and expansion of pancreatic β-cell mass.

11 Claims, 19 Drawing Sheets

AUC: 24028 ± 1519 (tg) vs. 19248 ± 1402 (wt); p < 0.05

AUC (-10 to 45): 1932 ± 187 (tg) vs. 2783 ± 247 (wt); p < 0.05

AUC: 13562 ± 359 (tg) vs. 14315 ± 651 (wt); p = 0.663

AUC: 1135 ± 111 (tg) vs. 1254 ± 269 (wt); p = 0.664

| Test | Group | Time | Group*Time |
|---|---|---|---|
| IVGTT | F-value 1,13 (P-value 0,29) | F-value 12,45 (P-value <0,0001) | F-value 0,15 (P-value 0,99) |
| IVGTT + GIP | F-value 6,4 (P-value 0,013) | F-value 24,01 (P-value <0,0001) | F-value 1,16 (P-value 0,32) |
| IVGTT + Exendin-4 | F-value 14,01 (P-value 0,0003) | F-value 22,66 (P-value <0,0001) | F-value 2,04 (P-value 0,03) |

FIG. 9C

TRANSGENIC PIG WITH ALTERED INCRETIN FUNCTION

CROSS-REFERENCE TO A RELATED APPLICATION

This application claims the benefit of U.S. provisional application Ser. No. 61/019,001, filed Jan. 4, 2008. This application also claims priority to European Application No. 08 000 111, filed Jan. 4, 2008, both of which are incorporated herein by reference in their entirety.

FIELD OF THE INVENTION

The present invention relates to transgenic pigs containing a dominant-negative incretin hormone receptor, namely the dominant-negative human glucose-dependent insulinotropic polypeptide receptor. The present invention furthermore relates to uses of these transgenic pigs as clinically relevant animal model systems for studying the pathogenesis and novel therapies for diabetes mellitus type 2, particularly for the maintenance and expansion of pancreatic β-cell mass.

BACKGROUND OF THE INVENTION

The incretin hormones glucose-dependent insulinotropic polypeptide (GIP) and glucagon-like peptide-1 (GLP-1) are secreted by enteroendocrine cells in response to nutrients like fat and glucose and enhance glucose-induced release of insulin from pancreatic β-cells (1,2). GIP and GLP-1 are both secreted within minutes of nutrient ingestion and facilitate the rapid disposal of ingested nutrients. Both peptides share common actions on islet β-cells acting through structurally distinct yet related receptors. Incretin-receptor activation leads to glucose-dependent enhancement of insulin secretion, induction of β-cell proliferation, and enhanced resistance to β-cell apoptosis. GIP also promotes energy storage via direct actions on adipose tissue, and enhances bone formation via stimulation of osteoblast proliferation and inhibition of bone resorption. GIP and GLP-1 are rapidly degraded by the enzyme dipeptidyl peptidase-4 (DPP-4).

The effects of GIP and GLP-1 are mediated through specific 7-transmembrane-domain G-protein coupled receptors, GIPR and GLP-1R, respectively (3). Activation of GIPR or GLP-1R is coupled to increases in cAMP and intracellular $Ca^{2+}$ levels, as well as activation of PI-3K, Epac 2, PKA, PKB, MAPK and phospholipase A2 and finally leads to enhanced exocytosis of insulin-containing granules (4).

In diabetes mellitus type 2 (T2D), a chronic metabolic disorder characterized by insulin resistance and progressive dysfunction of pancreatic islet cells, the meal-stimulated insulin secretion from β-cells is reduced and fails to meet the demands of the insulin-resistant state. Interestingly, the insulinotropic action of the incretin hormone glucose-dependent insulinotropic polypeptide (GIP) is impaired in type 2 diabetic patients while the effect of glucagon-like peptide-1 (GLP-1) is vastly preserved (1, 10).

Findings in insulinoma cells (5-7) and rodent models (8, 9) indicate that activation of the incretin receptors promotes proliferation and survival of β-cells. This observation as well as studies demonstrating that only the insulinotropic effect of GIP is greatly reduced while GLP-1 functions normally (1) initiated the ongoing development of incretin-based therapies such as incretin mimetics, GLP-1 analogues and inhibitors of the enzyme dipeptidyl-peptidase-4 (DPP-4), which inactivates incretins (reviewed in (2)). The reasons for the reduced response to GIP in T2D are unclear, but it was suggested that impaired GIP action might be involved in the early pathogenesis of type 2 diabetes mellitus (10).

DE 198 36 382 C2 discloses a transgenic mouse containing an altered GIPR which binds GIP but does not induce signalling after binding GIP (11). The transgenic mice expressing the altered GIPR in the β-cells of the pancreas develop a severe diabetes during the first month of their lives (11). Due to this early onset of diabetes, no long-term studies of disturbed GIP/GIPR function in the absence of glucose toxicity can be performed in the mouse model.

Thus, there is a need in the art for improved tools and methods for studying diabetes mellitus, in particular the role of GIP and the involvement of its impaired insulinotropic action in the pathogenesis of type 2 diabetes mellitus (T2D).

BRIEF SUMMARY

Therefore, the problem to be solved by this invention was to provide such improved tools and methods, especially more clinically relevant animal models and uses thereof.

The problem is solved by the present invention by providing a transgenic pig.

The transgenic pig according to the present invention comprises a recombinant nucleic acid encoding a dominant-negative human glucose-dependent insulinotropic polypeptide receptor (hGIPR$^{dn}$).

BRIEF DESCRIPTION OF THE DRAWINGS

The following drawings and illustrate the present invention without, however, limiting the same thereto.

a: The lentiviral vector (LV-GIPR$^{dn}$) carrying the cDNA of the dominant-negative GIP-receptor (GIPR$^{dn}$) under the control of the rat insulin 2 gene promoter (RIPII); LTR: long terminal repeat; ppt: polypurine tract; W: woodchuck hepatitis posttranscriptional regulatory element; wavy lines: pig genome; SIN: self-inactivating mutation; ApaI: restriction site of ApaI; probe: probe used for Southern blot analyses.

b: Southern blot analyses of ApaI-digested genomic DNA isolated from EDTA blood of piglets generated by subzonal injection of LV-GIPR$^{dn}$ (tg) and two non-transgenic littermate control animals (wt); Pigs of the F0 generation show either one or two single-copy integration sites of the transgene; S 50/S 51: sires of the piglets shown in the Southern blot of the F1-generation as indicated by the grey (S 50) and the black (S 51) lines; pigs of the F1 generation show segregation of the integrants according to the mendelian rules.

c: Analysis of transgene expression (GIPR$^{dn}$) in isolated porcine islets of Langerhans of transgenic (tg) and non-transgenic littermate control animals (wt) by RT-PCR; β-actin RT-PCR used for confirmation of reverse transcription efficiency; due to the use of intron-spanning primers to detect β-actin two different-sized bands are visible differentiating cDNA and genomic DNA; M: pUC Mix Marker; −RT wt: minus RT wild-type pigs; −RT tg: minus RT GIPR$^{dn}$ transgenic pigs; wt: wild-type pigs 1 and 2; tg: GIPR$^{dn}$ transgenic pigs 1 and 2; +: genomic DNA of GIPR$^{dn}$ transgenic pig; −: aqua bidest.

Figure 2A:
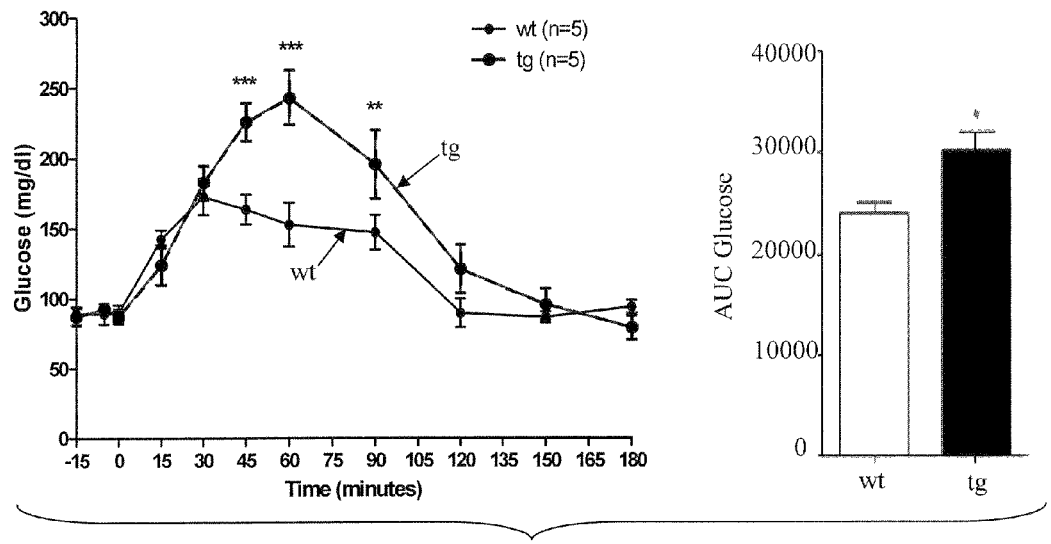
Figure 2B:
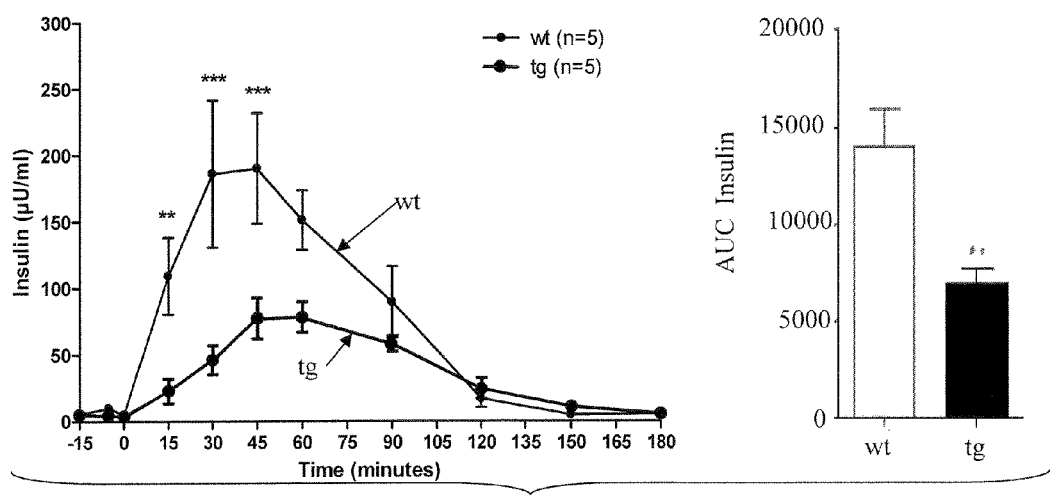

FIG. 2a-b. Impaired glucose tolerance and reduced initial insulin secretion in an oral glucose tolerance test of 5-month-old GIPR$^{dn}$ transgenic pigs (tg) and non-transgenic littermate control animals (wt).

a: Blood glucose levels (left); 0=point of glucose administration; AUC glucose: area under the glucose curve (right).

b: Serum insulin levels (left); 0=point of glucose administration; AUC insulin: area under the insulin curve (right).
Data are means±SEM; **: p<0.01 vs. control; *: p<0.05 vs. control.

FIG. 3. Functional analysis of GIPR$^{dn}$ expression in 28- to 36-week-old pigs.
a/b: Serum insulin levels a and Δ insulin values b of GIPR$^{dn}$ transgenic (tg) and control (wt) pigs after intravenous administration of glucose (Glc) w/o GIP.
c/d: Serum insulin levels c and Δ insulin values d of GIPR$^{dn}$ transgenic (tg) and control (wt) pigs after intravenous administration of glucose (Glc) w/o Exendin-4 (Exe-4).
b/d: Δ Insulin (µU/ml): difference of the maximum insulin level and the insulin level determined at three minutes after the intravenous glucose load (directly before GIP/Exendin-4 application); 0 minutes=point of glucose administration; 3 minutes=point of GIP/Exendin-4 administration.
Data are means±SEM; *: p<0.05 vs. control.

Figure 4A:
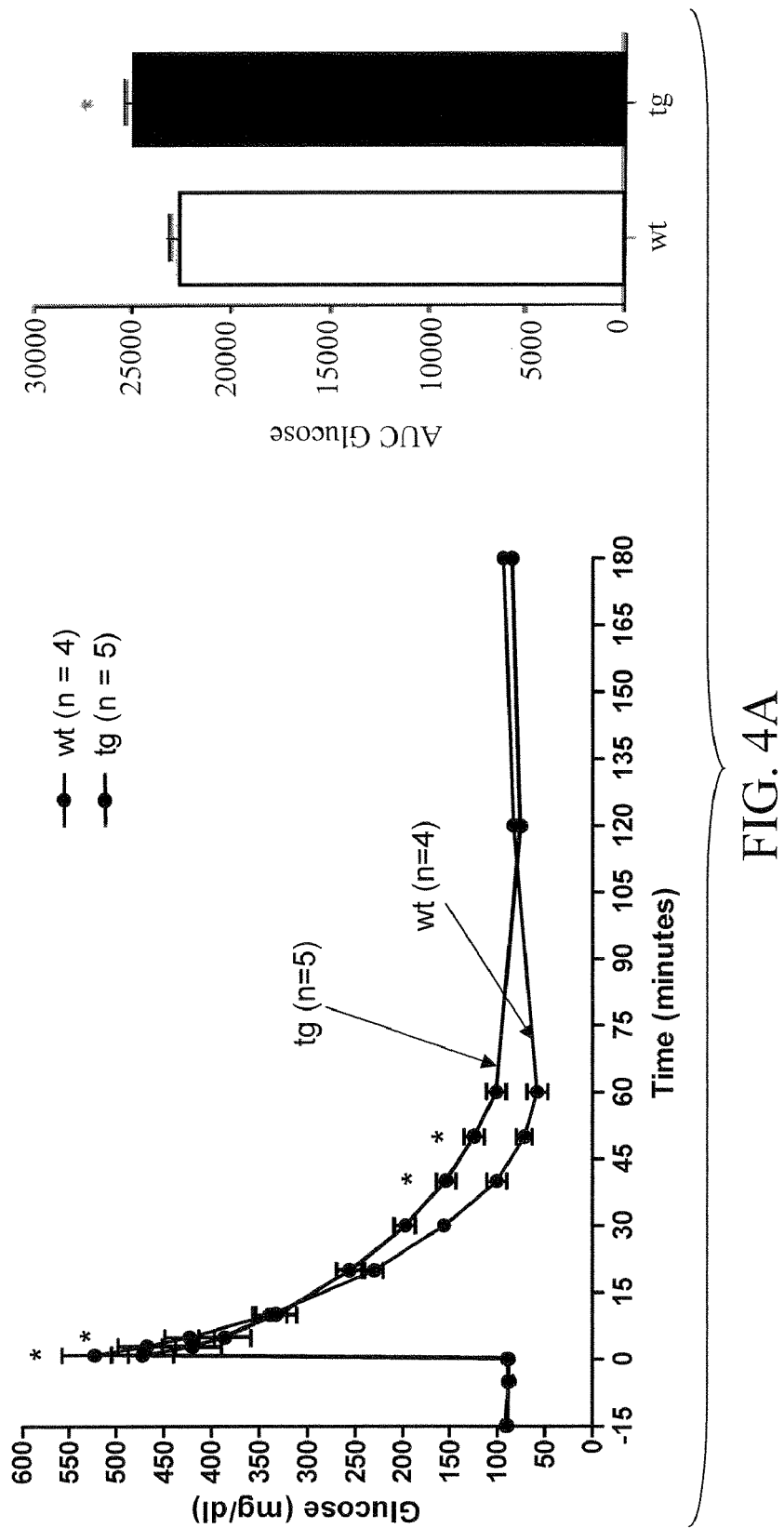
Figure 4B:
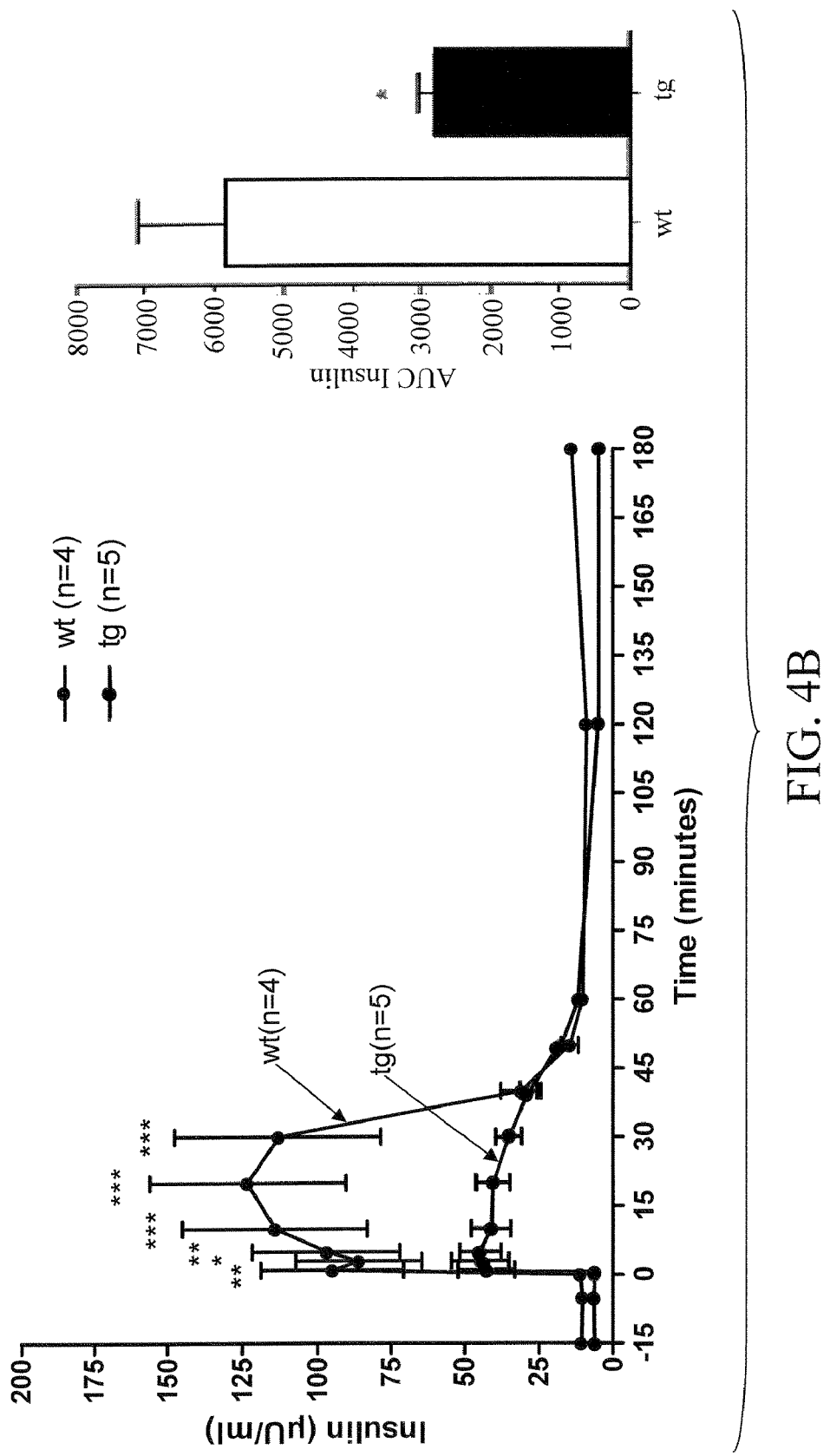

FIG. 4. Reduced intravenous glucose tolerance in 11-month-old GIPR$^{dn}$ transgenic pigs (tg) and non-transgenic littermate control animals (wt).
a: Blood glucose levels (left); 0=point of glucose administration; AUC glucose: area under the glucose curve (right).
b: Serum insulin levels (left); 0=point of glucose administration; AUC insulin: area under the insulin curve (right).
Data are means±SEM; *: p<0.05 vs. control.

Figure 5:
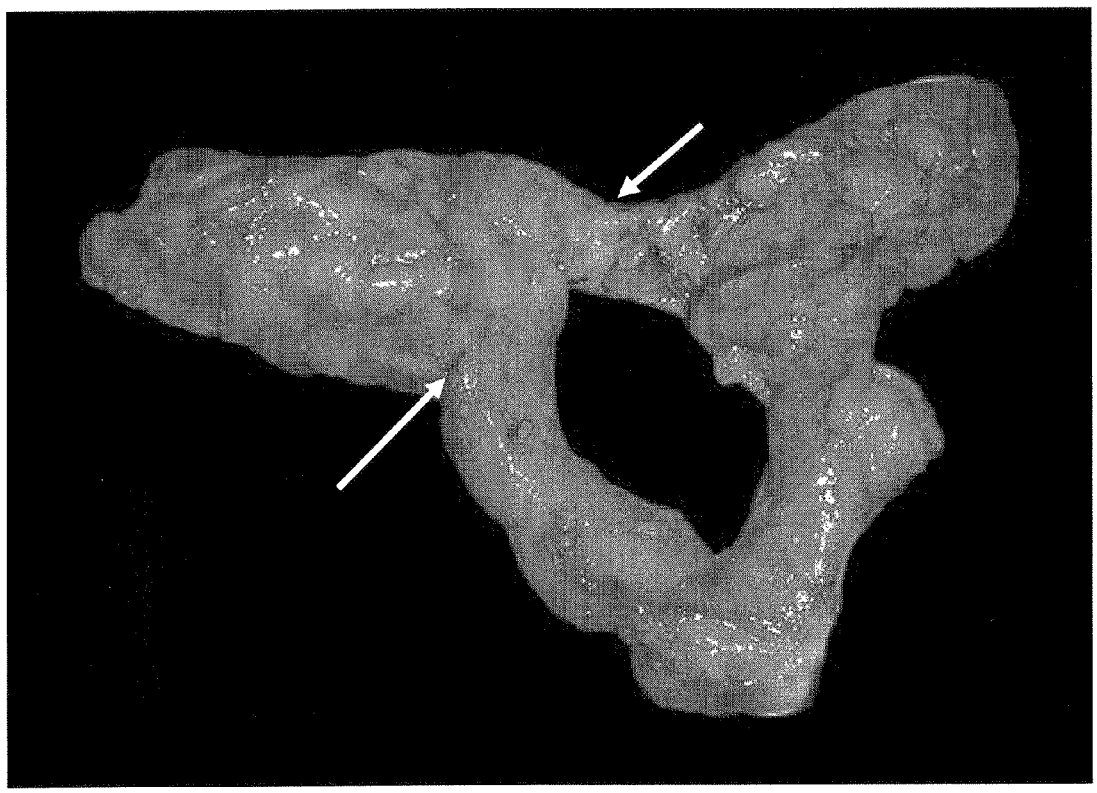

FIG. 5. Scheme of pancreas preparation for islet isolation and quantitative stereological analyses in young adult (1-1.4 years) pigs. White arrows indicate the separation site of the left pancreatic lobe from the rest of the organ using the left pancreatic lobe for islet isolation and the remnant organ for quantitative stereological analyses.

FIG. 6. Reduced total β-cell volume in young adult (1-1.4 years) GIPR$^{dn}$ transgenic pigs (tg) and non-transgenic control animals (wt).
a: Representative histological sections of pancreatic tissue from a control (wt) and a GIPR$^{dn}$ transgenic pig (tg); note the markedly reduced size of islet profiles in transgenic pigs; magnification 2.5×; scale bar=200 µm.
b,c: Quantitative stereological analyses of the pancreas of young adult (1-1.4 years) pigs;
b: Total β-cell volume ($V_{(β-cell, Pan)}$);
c: Total volume of isolated β-cells ($V_{(iso\ β-cell, Pan)}$).
Data are means±SEM; **: p<0.01 vs. control.

FIG. 7. Impaired oral glucose tolerance, but normal intravenous glucose tolerance in an oral/intravenous glucose tolerance test of 11-week-old GIPR$^{dn}$ transgenic pigs (tg) and non-transgenic control animals (wt).
a,b: Oral glucose tolerance test;
a: Serum glucose levels; 0 minutes=point of glucose administration;
b: Serum insulin levels.
c,d: Intravenous glucose tolerance test;
c: Serum glucose levels; 0 minutes=point of glucose administration;
d: Serum insulin levels.
AUC: area under the glucose/insulin curve for tg pigs (red) and wt pigs (blue).
Data are means±SEM; *: p<0.05 vs. control.

Figure 8A:
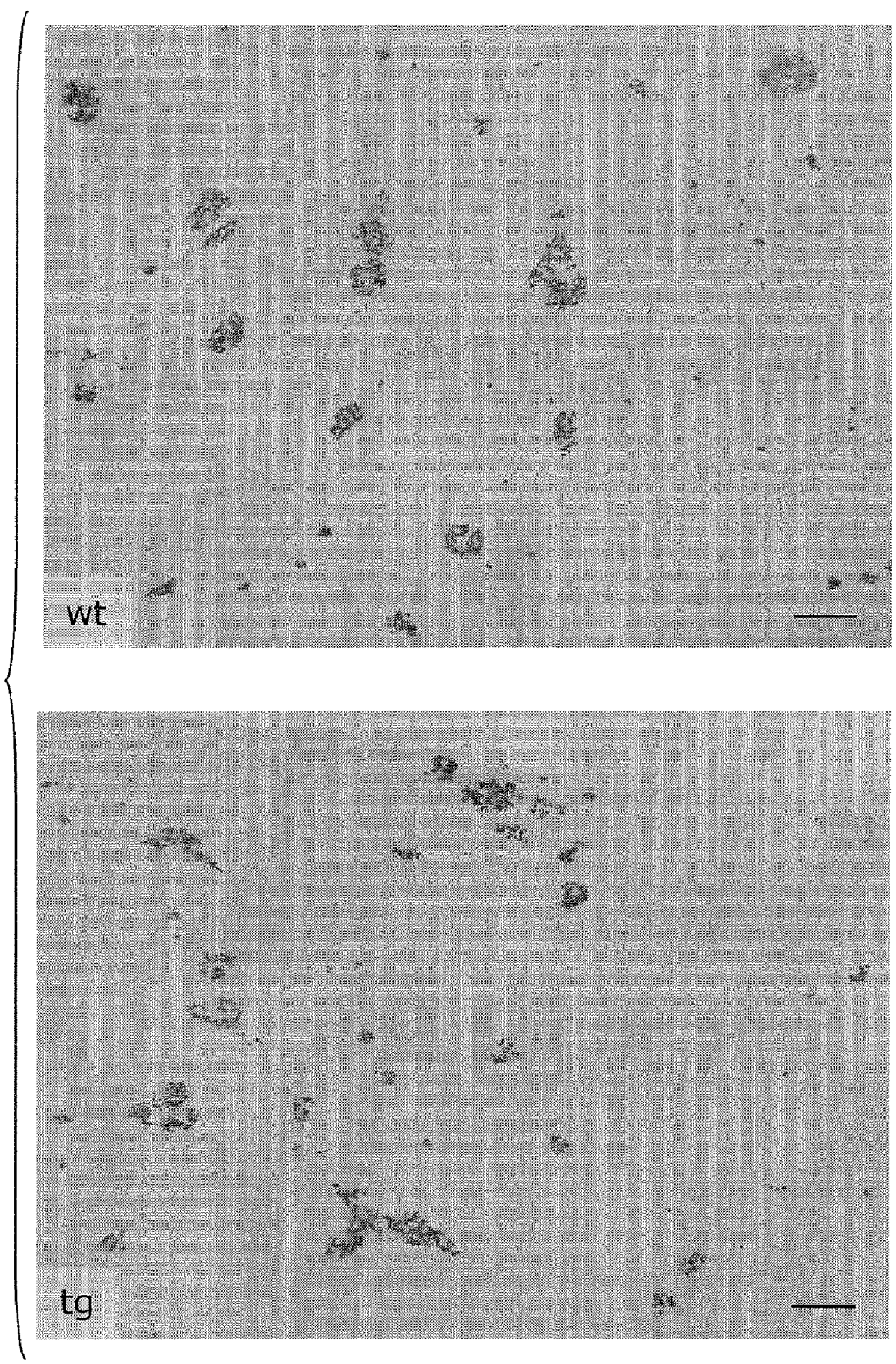

FIG. 8. Unaltered total β-cell volume in 11-week-old GIPR$^{dn}$ transgenic pigs (tg) and non-transgenic control animals (wt).
a: Representative histological sections of pancreatic tissue from a control (wt) and a GIPR$^{dn}$ transgenic pig (tg); magnification 2.5×; scale bar=200 µm.
b,c: Quantitative stereological analyses of the pancreas of 11-week-old pigs;
b: Total β-cell volume ($V_{(β-cell, Pan)}$);
c: Total volume of isolated β-cells ($V_{(iso\ β-cell, Pan)}$).
Data are means±SEM.

FIG. 9. Functional analysis of GIPR$^{dn}$ expression in 10- to 13-week-old pigs showing an impaired insulinotropic effect of GIP, but enhanced insulinotropic effect of Exendin-4 in GIPR$^{dn}$ transgenic pigs compared to controls.
a: Serum insulin levels of GIPR$^{dn}$ transgenic (tg) and control (wt) pigs after intravenous administration of glucose (Glc) w/o GIP.
b: Serum insulin levels of GIPR$^{dn}$ transgenic (tg) and control (wt) pigs after intravenous administration of glucose (Glc) w/o Exendin-4 (Exe-4).
c: Results of Analysis of Variance (ANOVA). 0 minutes=point of glucose administration; 0 minutes=point of GIP/Exendin-4 administration.

| Test | Group | | Time | | Group * Time | |
|---|---|---|---|---|---|---|
| | F-value | P-value | F-value | P-value | F-value | P-value |
| IVGTT | 1.13 | 0.29 | 12.45 | <0.0001 | 0.15 | 0.99 |
| IVGTT + GIP | 6.4 | 0.013 | 24.01 | <0.0001 | 1.16 | 0.32 |
| IVGTT + Exendin 4 | 14.01 | 0.0003 | 22.66 | <0.0001 | 2.04 | 0.03 |

Data are means±SEM; **: p<0.01 vs. control.

Figure 10A:
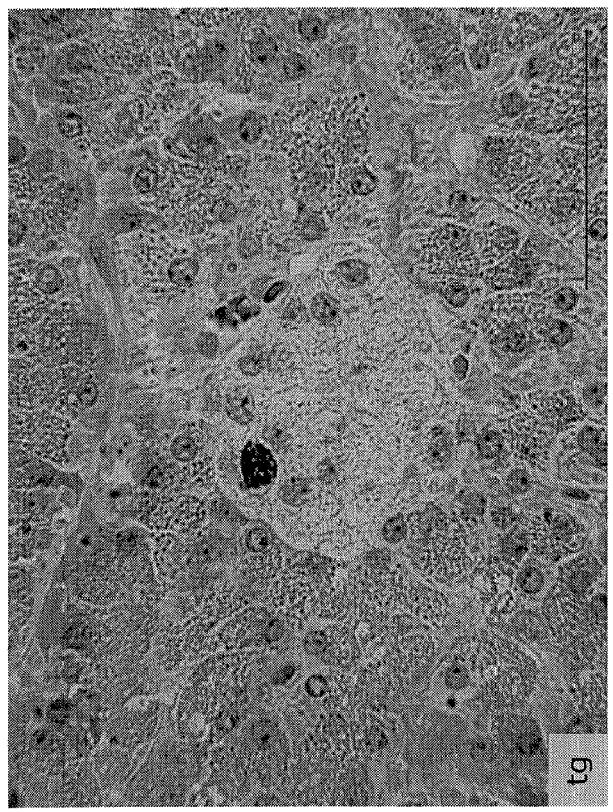
Figure 10A:
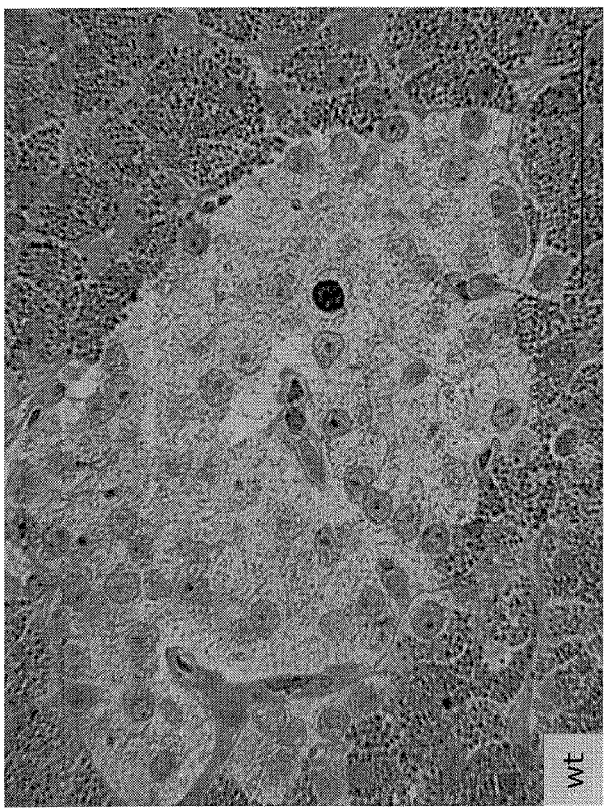
Figure 10B:
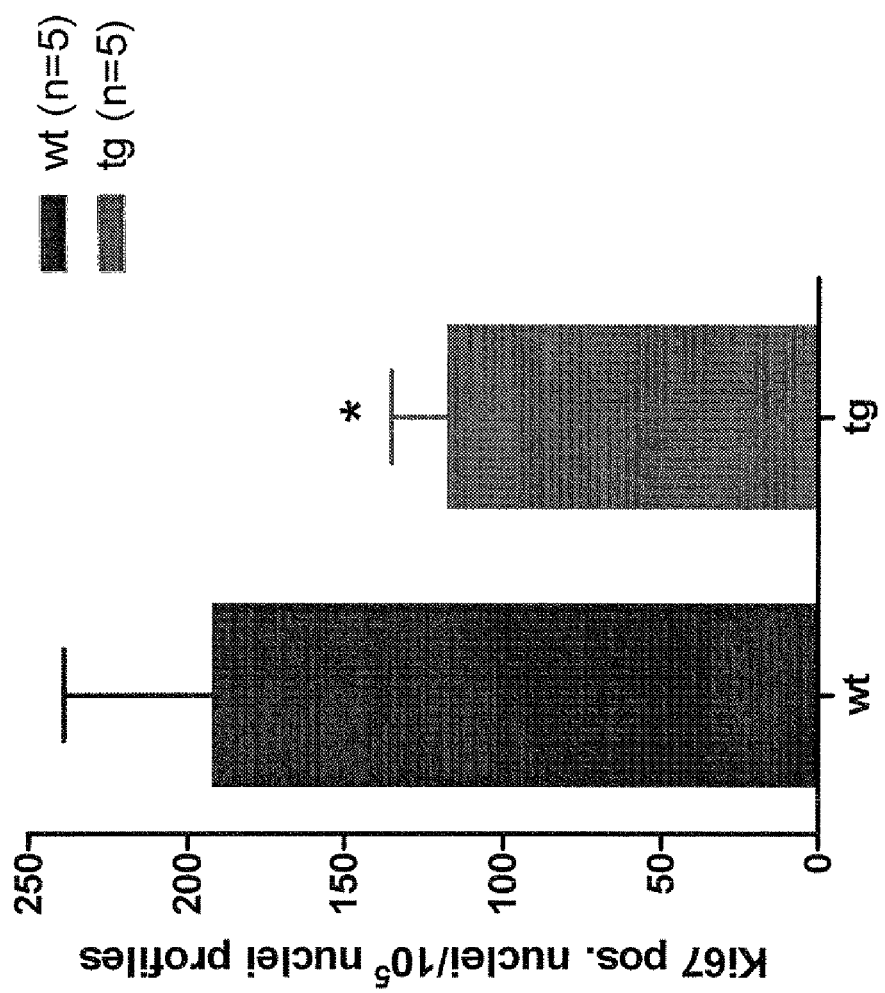

FIG. 10. Reduced proliferation of islet cells in young adult (1-1.4 years old) GIPR$^{dn}$ transgenic pigs (tg) compared to non-transgenic control animals (wt).
a: Representative histological sections of pancreatic tissue (immunohistochemical staining with an anti-Ki67 antibody in combination with H.E. staining) from a control (wt) and a GIPR$^{dn}$ transgenic pig (tg); magnification 40×; scale bar=50 µm.
b: Number of Ki67 positive nuclei per 105 nuclei profiles.
Data are means±SEM; *: p<0.05 vs. control.

BRIEF DESCRIPTION OF THE SEQUENCES

SEQ ID NO:1 is an amino acid useful according to the subject invention.
SEQ ID NO:2 is a cDNA sequence useful according to the subject invention.
SEQ ID NO:3 is a primer sequence useful according to the subject invention.
SEQ ID NO:4 is a primer sequence useful according to the subject invention.

DETAILED DISCLOSURE

A "nucleic acid" according to the invention refers to polynucleotides, such as DNA, RNA, modified DNA, modified RNA as well as mixtures thereof.

A "dominant-negative" GIP receptor according to this invention refers to a modified GIPR which binds the ligand GIP but is not capable of signal transduction. This dominant-negative receptor competes with the endogenous intact GIP receptor for the ligand GIP and—depending on the level of expression of the dominant-negative receptor—impairs the function of GIP.

Preferably, the recombinant nucleic acid encodes a protein which comprises an eight amino acid deletion (residues 319-326) and an amino acid change at residue 340, preferably Ala to Glu, in the third intracellular loop of the hGIPR.

More preferably, the recombinant nucleic acid encodes a protein comprising SEQ ID NO: 1 or having SEQ ID NO: 1.

Preferably, the recombinant nucleic acid comprises SEQ ID NO: 2, the cDNA sequence corresponding to SEQ ID NO: 1.

Preferably, the recombinant nucleic acid encoding hGIPR$^{dn}$ is comprised in a plasmid or viral vector. A preferred viral vector is a lentiviral vector.

However, any other method for introducing the expression vector into early embryos is possible. Alternatively, the expression vectors can be introduced into somatic cells which will then be used for nuclear transfer to generate cloned transgenic animals.

The plasmid or viral vector comprises a promoter which allows for expressing the hGIPR in the transgenic pig, preferably allows expression in the pancreatic islets, preferably the β-cells of the pancreas.

A preferred promoter is an insulin promoter, more preferably rat insulin 2 gene promoter (RIPII). Further suitable promoters are the pig INS promoter or other promoters which confer expression in the pancreatic islets, such as PDX1.

In an embodiment of the invention, promoters with other tissue specificities are used to evaluate the role of GIP receptor function in other GIP target tissues, such as adipose tissue, bone, and brain.

Preferably, the recombinant nucleic acid is a lentiviral vector comprising the rat insulin 2 gene promoter (RIPII).

Figure 1A:
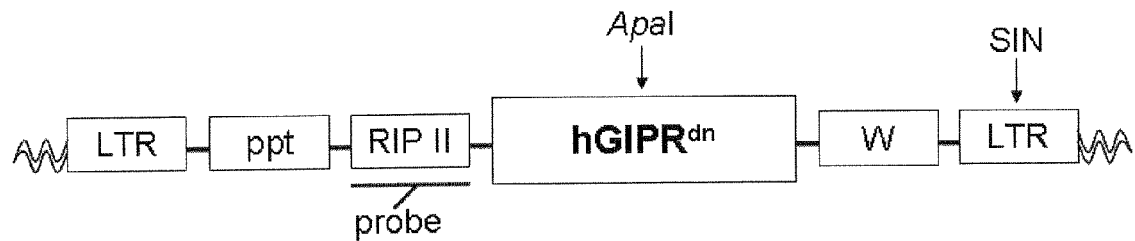
FIG. 1a-c. Lentiviral vector, Southern blot analyses and transgene expression.

A preferred viral construct is shown in FIG. 1a.

Preferably, the hGIPR$^{dn}$ is expressed in the islets of the pancreas, preferably the β-cells.

Preferably, the hGIPR$^{dn}$ is overexpressed in the islets of the pancreas, preferably the β-cells, of the transgenic pig compared to wild-type hGIPR.

The transgenic pig according to the present invention preferably contains the recombinant nucleic acid encoding hGIPR$^{dn}$ in its germ cells and somatic cells.

Thus, transgenic cell lines can be established by breeding to generate a standardized model system for metabolic research, particularly in the context of diabetes.

Preferably, the recombinant nucleic acid encoding hGIPR$^{dn}$ is integrated into the genome of the transgenic pig.

Preferably, the transgenic pig exhibits elevated glucose levels following an oral glucose load as well as distinct reduction of insulin secretion. The transgenic pig exhibits a reduced oral glucose tolerance.

Preferably, pancreatic islet and β-cell mass of the transgenic pig is reduced.

However, at the time of birth the transgenic pigs of the present invention do not show a reduction of the pancreatic β-cell mass. As in the disease, in particular diabetes mellitus type 2, the pancreatic islet and β-cell mass is reduced over time, as can be seen from the results of the Examples. Also at an early age, such as 11 weeks, the transgenic pigs of the invention do not have a reduced β-cell mass (see e.g. FIG. 8). However, the pancreatic islet and β-cell mass is markedly reduced in young adult transgenic pigs, such as 1- to 1.4-year old transgenic pigs, (see e.g. FIG. 6). Therefore, the changes in pancreatic β-cell mass and functionality of the transgenic pigs are progressive in nature. Thus, the present invention provides an ideal model for studying the pathogenesis of diabetes (such as by studying the involvement of the GIP/GIPR axis in the pathogenesis of diabetes), for studying and identifying compounds and other means that influence the β-cell mass reduction.

The volume density of β-cells in the pancreas ($Vv_{(\beta\text{-}cell/Pan)}$) are preferably reduced in young adult GIPR$^{dn}$ transgenic pigs vs. controls. Accordingly, the total volume of β-cells ($V_{(\beta\text{-}cell,Pan)}$; see FIG. 6b) is preferably reduced in young adult GIPR$^{dn}$ transgenic pigs compared to non-transgenic controls. However, volume density as well as the total volume of isolated β-cells ($Vv_{(iso\beta\text{-}cell/Pan)}$, $V_{(iso\beta\text{-}cell,Pan)}$) are preferably not different between the two groups, suggesting that impaired GIP signaling affects islet (β-cell) maintenance but not neogenesis of pancreatic (β-cell) islets.

The problem is furthermore solved by the present invention by providing a transgenic cell or transgenic cell line from a transgenic pig of the present invention.

According to the invention a transgenic cell or cell line is obtained from a transgenic pig of the invention.

Preferably, the transgenic cell or cell line is obtained from a germ cell and/or a somatic cell of said transgenic pig.

The skilled person is able to determine suitable methods and procedures for obtaining transgenic cells or cell lines from the transgenic pigs.

The transgenic cells and/or cell lines are suitable in vitro test systems and can be used for developing autologous cell replacement therapies.

Preferably the transgenic cells and/or cell lines can be used to generate a standardized model system for metabolic research, particularly in the context of diabetes.

In preferred embodiments, the transgenic cells or cell lines are used as in vitro test systems of diabetes mellitus (preferably T2D) and/or for generating a model system for metabolic research, preferably in the context of diabetes mellitus (more preferably T2D).

The transgenic cells and/or cell lines, preferably respective somatic cells/cell lines, can also be used to obtain transgenic pigs, such as by cloning strategies.

Uses of the Transgenic Pigs, in Particular as Diabetes Model

The problem is furthermore solved by the present invention by using a transgenic pig according to the present invention in studying and therapy/treatment of diabetes, in particular diabetes mellitus type 2.

Preferably, the transgenic pigs of the present invention are used as model system for the pathogenesis of diabetes mellitus, in particular diabetes mellitus type 2, i.e. for studying the pathogenesis and onset of diabetes, in particular the pancreatic islet mass reduction.

The "pathogenesis" of diabetes mellitus, in particular diabetes mellitus type 2 comprises the onset and development and progress of this disease.

Preferably, the transgenic pigs of the present invention are used as model system for the therapy or treatment of diabetes mellitus, in particular diabetes mellitus type 2, i.e. for identifying means and methods suitable for the therapy or treatment of diabetes mellitus, in particular diabetes mellitus type 2.

"Diabetes mellitus type 2" (formerly called diabetes mellitus type II, non insulin-dependent diabetes (NIDDM), obesity related diabetes, or adult-onset diabetes) according to the present invention refers to a metabolic disorder that is primarily characterized by insulin resistance, relative insulin deficiency, and hyperglycemia. It is rapidly increasing in the developed world, and there is some evidence that this pattern will be followed in much of the rest of the world in coming years. Unlike type 1 diabetes, there is little tendency toward ketoacidosis in type 2 diabetes. One effect that can occur is nonketonic hyperglycemia. Complex and multifactorial metabolic changes lead to damage and function impairment of many organs, most importantly the cardiovascular system in both types. This leads to substantially increased morbidity and mortality in both type 1 and type 2 patients, but the two have quite different origins and treatments despite the similarity in complications.

The transgenic pigs according to the present invention are a highly suitable animal model system for diabetes mellitus because, as described herein, they exhibit the following key features of diabetes mellitus type 2: impaired incretin effect, glucose intolerance and reduction of pancreatic β-cell mass.

Importantly, the transgenic pigs of the present invention at the time of birth and at an early age (e.g. at 11 weeks) do have a disturbed/impaired incretin function leading to an impaired oral glucose tolerance and delayed insulin secretion, but do neither already have an impaired intravenous glucose tolerance nor a reduction of pancreatic β-cell mass. They will develop these characteristic features of diabetes during their lifetime and show as young adults (e.g. at 1-1.4 years) a reduced pancreatic β-cell mass as well as impaired intravenous glucose tolerance (wherein intravenous glucose tolerance test was performed at 11 month of age, see below).

The transgenic pig model furthermore overcomes the limitations of the mouse model, as e.g. disclosed in DE 198 36 382 C2.

A known transgenic mouse, as e.g. disclosed in DE 198 36 382 C2, contains an altered GIPR which binds GIP but does not induce signalling after binding GIP. The transgenic mice expressing the altered GIPR in the β-cells of the pancreas develop a severe diabetes during the first month of their lives. However, stimulation studies with GIP or GLP-1 could not reveal significant results in the mouse model due to its limited size and the early onset and especially the high-grade of pancreatic islet mass reduction. Thus, it cannot be assessed whether the unexpected severe phenotype is due to specific inhibition of the GIP effect or due to a mere unspecific disturbance of the β-cells due to a high level of overexpression of the dominant-negative receptor which may cause—in part—non-specific effects, e.g. by squelching of G-proteins. In addition, due to the early onset of diabetes in the mouse models, no long-term studies of disturbed GIP/GIPR function in the absence of glucose toxicity can be performed. Further, the number and volumes of blood samplings in the mouse are limited, precluding dose-response studies with a high resolution in time. Finally, the endocrine and metabolic functions are more similar between pig and human as compared to mouse and human, rendering the pig an ideal model system for metabolic studies.

With the transgenic pigs of the present invention, for the first time a transgenic large animal model with impaired incretin function is established.

The use of the transgenic pigs preferably comprises the evaluation of the role of impaired GIP signalling in the pathogenesis of diabetes mellitus, in particular diabetes mellitus type 2.

This can be done, for instance, by profiling of signalling mechanisms in isolated pancreatic islets and pharmacological intervention studies.

The use preferably comprises the characterization of the mechanisms by which GIP supports pancreatic islet maintenance in vivo.

The use preferably comprises the development and evaluation of incretin-based therapeutic strategies of diabetes mellitus, in particular diabetes mellitus type 2.

An example is already provided by the Exendin-4 treatment study, as described herein below. Different treatment regimens can be evaluated with regard to efficacy and safety. Important readouts will be the dynamics of insulin secretion (which can only be determined with the required high resolution in time in a large animal model) and effects on pancreatic islet mass.

In a preferred embodiment of the present invention, a transgenic pig is used as model system for the pathogenesis and/or therapy/treatment of diabetes mellitus, in particular diabetes mellitus type 2, wherein the use comprises monitoring the pancreatic islet mass and β-cell mass over time, such as in time intervals or in a continuous manner.

Thereby, "over time" refers to over the lifetime of a transgenic pig or over a certain period of time during the life of a transgenic pig. "Over time" can also refer to a period of time starting from a stimulus that is administered to the transgenic pig, starting from the time point where a compound is administered to the transgenic pig or the like.

The time intervals are preferably monthly, two week intervals or even weekly intervals. The skilled artisan is able to chose further suitable time intervals.

Monitoring the pancreatic islet mass and β-cell mass, as in the uses and methods of the present invention, comprises in vivo monitoring and/or in vitro monitoring (wherein in vitro monitoring comprises also post-mortem studies and methods).

Monitoring the pancreatic islet mass and β-cell mass, as in the uses and methods of the present invention, comprises the following steps and methods:
(i) Labelling and Imaging Preferably by labelling of pancreatic islets, β-cells and/or non-β-cells (within islets) and detecting the label(s).

This is preferably an in vivo method, however in vitro applications are also possible.

The compounds and molecules used for labelling pancreatic islets, β-cells and/or non-β-cells (within islets) preferably comprise a detectable label and a part/moiety which is specific for the pancreatic islets, β-cells and/or non-β-cells (within islets).

Detectable labels (in particular detectable labels suitable for in vivo use and for use in animals) are known in the art, such as radioisotopes (such as $^{131}$I), chromogenic compounds, fluorogenic compounds, enzyme substrates.

The part/moiety of the compounds and molecules which is specific for the pancreatic islets, β-cells and/or non-β-cells within islets can preferably be selected from
- ligands, preferably specific for pancreatic islets, β-cells and/or non-β-cells within islets
  (such as their receptors or other (surface) molecules), such as GLP-1R ligand;
  (wherein ligands also comprises agonists, antagonists, mimetics etc),
- metabolites (of pancreatic islets, β-cells and/or non-β-cells) or metabolic markers
  for example
  β-cells: insulin; non-β-cells: glucagon (A/α-cells), somatostatin (D/δ-cells), pancreatic polypeptide (F/PP-cells);
- antibodies and/or antibody fragments and/or other (high affinity) binding molecules (specific for pancreatic islets, β-cells and/or non-β-cells, such as by specifically binding to their receptors or other (surface) molecules/metabolites)
  for example
   antibodies: β-cells: anti-insulin antibody; non-β-cells: anti-glucagon antibody (A/α-cells), anti-somatostatin antibody (D/δ-cells), anti-pancreatic polypeptide antibody (F/PP-cells), anti-GIPR antibody, anti-GLP-1 receptor antibody,
   lipocalins and their derivatives/fragments/variants etc, such as Anticalins®
- other specific binding molecules:
  for example
   dithizone and its derivatives, (dithizone, a chelate/complexing agent) which selectively stains β-cells due to their high zinc content in insulin granules)

such as mono and diiodo-derivatives of dithizone labelled with radioactive $^{131}$I isotope or other labelled forms of dithizone which selectively stains β-cells due to their high zinc content in insulin granules;

Further parts/moieties can be designed, chosen and/or selected by a skilled artisan.

Overviews of potential in vivo labelling and imaging techniques for pancreatic islets or β-cells have been published recently (see for example 33 und 34).

The labels are preferably detected by imaging methods, preferably in vivo imaging methods, which are chosen/selected depending on the label to be detected. Such imaging methods are known to the skilled artisan and include high resolution multi-pinhole SPECT (single photon emission computed tomography).

In vitro imaging methods are known to the skilled artisan and include, immunohistochemistry, immunofluorescence and other histological staining techniques.

Preferably, a verification/validation of the detected signal of the label(s) is carried out in vitro, preferably by post mortem determination of the volume density of β-cells and/or non-β-cells in the islets/pancreas, and/or the total volume of β-cells and/or non-β-cells in the islets/pancreas, Such post mortem determinations are preferably by stereological means, such as on histological sections.

(ii) Determining the Volume Density of β-Cells or Non-β-Cells or Islets and/or the Total Volume of β-Cells or Non-β-Cells or Islets Methods for determining the volume density of β-cells or non-β-cells (within islets) or islets and/or the total volume of β-cells or non-β-cells (within islets) or islets are known to the skilled artisan; and include in vivo as well as in vitro methods.

A preferred in vivo method includes: high-resolution multi-pinhole SPECT (single photon emission computed tomography), such as after treatment with (radio)labeled GLP-1R ligand or other specific ligands or other detectable/labelled compounds and molecules, e.g. as the above.

Preferred in vitro methods include: stereological methods, preferably quantitative stereological analysis, such as described below and in the Examples herein.

(iii) Determining the Proliferation Rate and/or Apoptosis Rate

Here, the proliferation rate and/or apoptosis rate of pancreatic islets, β-cells and/or non-β-cells (within islets) is determined.

This is preferably an in vitro method utilizing specific (cell) proliferation markers and/or apoptosis markers, e.g. (labelled) antibodies etc, on histological sections, such as described in the Examples and for FIG. 10.

Examples for Proliferation Markers:

BrdU (5-Bromo-2'-deoxyuridine, preferably for in vivo labelling and post-mortem immunohistochemical detection);
Ki67 (preferably for post-mortem immunohistochemical detection);
PCNA (Proliferating Cell Nuclear Antigen, preferably for post-mortem immunohistochemical detection).

Examples for Apoposis Markers:

(activated) caspase-3 (preferably for post-mortem immunohistochemical detection);
TUNEL (Terminal deoxynucleotidyl transferase dUTP nick end labeling) assay (preferably for post-mortem immunohistochemical detection).

Furthermore, the present invention provides an ideal model for the development of techniques for dynamic monitoring of pancreatic islet mass.

Thus, the transgenic pigs of the invention can preferably be used for developing a method for monitoring the pancreatic islet mass and β-cell mass. Such a method is preferably an imaging method, more preferably an in vivo imaging method.

Suitable approaches combine specific in vivo labelling of pancreatic islets, β-cells and or non-β-cells (within islets) with respective labels and detecting the labels with suitable imaging technologies. Preferred labels and molecules/compounds etc are as described above.

Such a method can also be suitable for the dynamic (in vivo) monitoring of pancreatic islet mass, β-cell mass and/or non-β-cell mass within an islet in patients, in particular diabetes mellitus type 2 patients.

Methods Utilizing the Transgenic Pigs

The problem is furthermore solved by the present invention by providing methods which utilize the transgenic pigs of the present invention.

In a preferred embodiment, a method for studying the pathogenesis and/or the therapy/treatment of diabetes mellitus, in particular diabetes mellitus type 2, is provided.

Such a method preferably comprises the following steps (a) providing a transgenic pig according to the present invention, (b) monitoring the pancreatic islet mass and β-cell mass in said transgenic pig in time intervals or in a continuous manner, (c) optional, determining insulin secretion.

Step (b) comprises preferably in vivo monitoring the pancreatic islet mass and β-cell mass in said transgenic pig. Preferred time intervals are as described herein (monthly, two week intervals or even weekly intervals or others).

The insulin secretion is preferably determined by:

determining insulin secretion in response to an oral or intravenous glucose load,
determining the incretin effect
and/or
determining the insulinotropic effect of the incretin hormones (GIP or GLP-1 or their agonists, antagonists and/or mimetics and/or inhibitors of their degradation).

The incretin effect is determined by comparing insulin secretion following an oral glucose load with insulin secretion following an isoglycemic intravenous glucose load. For more details, see below and Examples.

The "incretin effect" according to the invention refers to a significantly greater insulin stimulatory effect evoked after an oral glucose load than that evoked from an intravenous glucose infusion when plasma glucose concentrations are matched.

The insulinotropic effect of the incretin hormones is preferably determined by using stimulation studies with the incretin hormones or by comparing the insulinotropic effect between the two (groups of) incretin hormones.

The two incretin hormones are:

GIP (glucose-dependent insulinotropic polypeptide) and
GLP-1 (glucagon-like peptide-1).

In the above methods, GIP or GLP-1 or their respective agonists, antagonists and/or mimetics and/or inhibitors of their degradation can be used.

For more details, see below and Examples.

The in vivo and/or in vitro monitoring of the pancreatic islet mass and β-cell mass is as described above.

In a further preferred embodiment, the method for studying the pathogenesis and/or the therapy/treatment of diabetes mellitus, in particular diabetes mellitus type 2, further comprises the following steps
(d) induction of and determining insulin resistance in said transgenic pig.
and/or
(e) determining the effect of stimuli or compounds on the pancreatic islet mass and β-cell mass and/or the insulin secretion (or insulin resistance) of said transgenic pig.

Methods for inducing insulin resistance in animals, such as a transgenic pig, are known in the art and comprise high caloric feeding. (31, 32).

In a further preferred embodiment, a method for identifying a compound that preferably modulates the incretin hormone system is provided.

A compound that modulates the incretin hormone system identified with the methods of the invention can ultimately also be suitable for preventing and/or treating diabetes, in particular T2D.

Such a method preferably comprises the following steps
(a) providing a transgenic pig according to the present invention,
(b) providing a compound to be tested,
(c) administering the compound to said transgenic pig,
(d) determining insulin secretion.

The insulin secretion is determined as described above.

Preferred administration routes of a compound are oral, nasal, subcutaneous, intracutaneous, parenteral, transdermal, topical, intravenous, intraarterial, intramuscular, intraperitoneal or combinations thereof.

In a preferred embodiment of the method for identifying a compound that modulates the incretin hormone system the method comprises the following steps
(a) providing a transgenic pig according to the present invention,
(b) monitoring the pancreatic islet mass and β-cell mass in time intervals or in a continuous manner,
(c) providing a compound to be tested,
(d) administering the compound to said transgenic pig,
(e) determining the effect of said compound on insulin secretion and/or the pancreatic islet mass and β-cell mass of said transgenic pig.

Step (b) comprises preferably in vivo monitoring the pancreatic islet mass and β-cell mass in said transgenic pig, as described above. Preferred time intervals are as described herein (monthly, two week intervals or even weekly intervals or others).

The compounds identified in this preferred embodiment can ultimately also be suitable for preventing and/or treating diabetes, in particular T2D,
such as by an influence on insulin secretion and/or the pancreatic islet mass and β-cell mass and its reduction. Preferably, such a compound is able to improve insulin secretion and/or prevent, slow down, inhibit and the like said reduction of pancreatic islet mass and β-cell mass.

Thus, the effect determined or measured in step (e) can be:
improvement of insulin secretion and/or
prevention or slowing down or inhibition of the reduction or rate of reduction of pancreatic islet mass and β-cell mass.

Figure 9A:
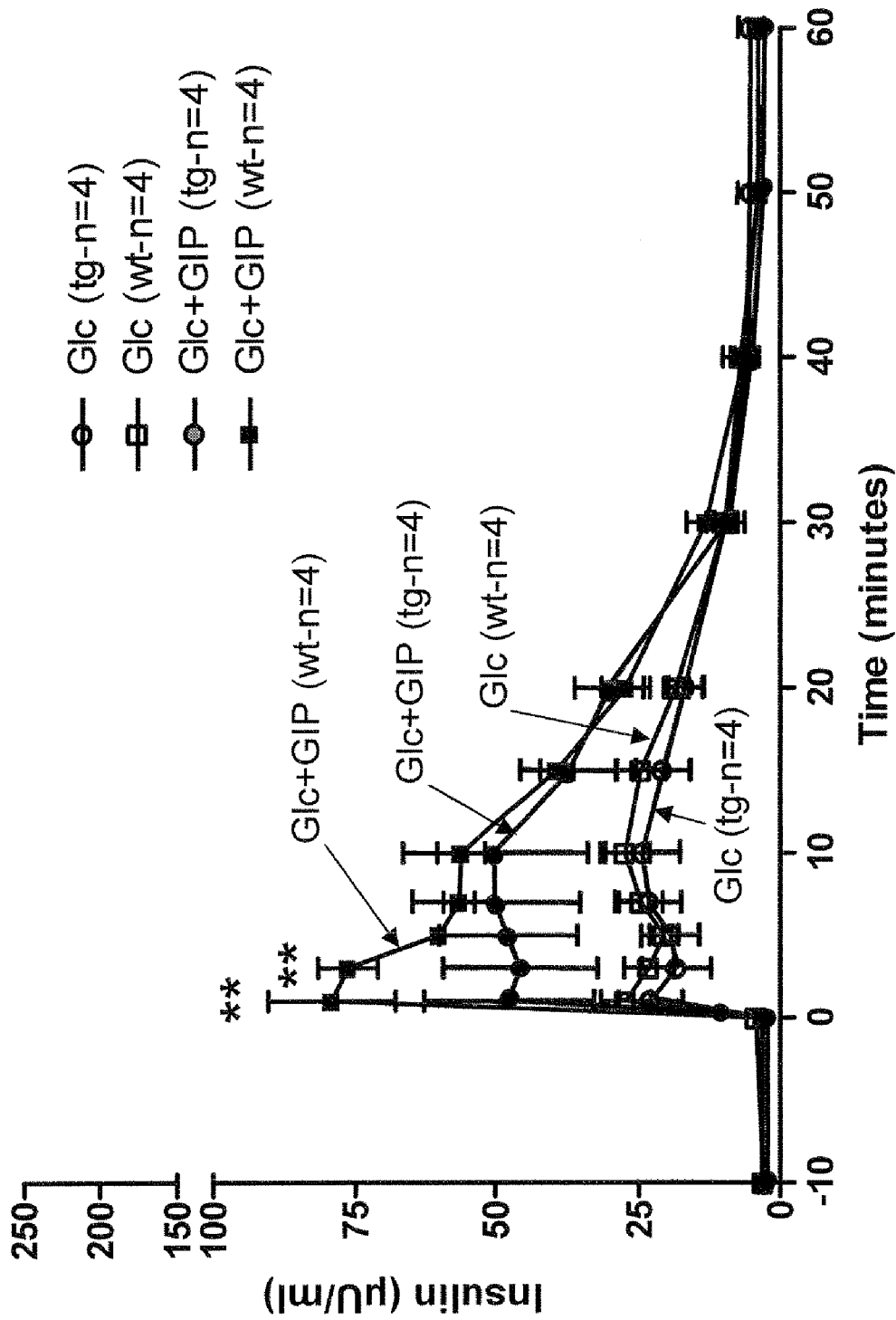
Figure 9B:
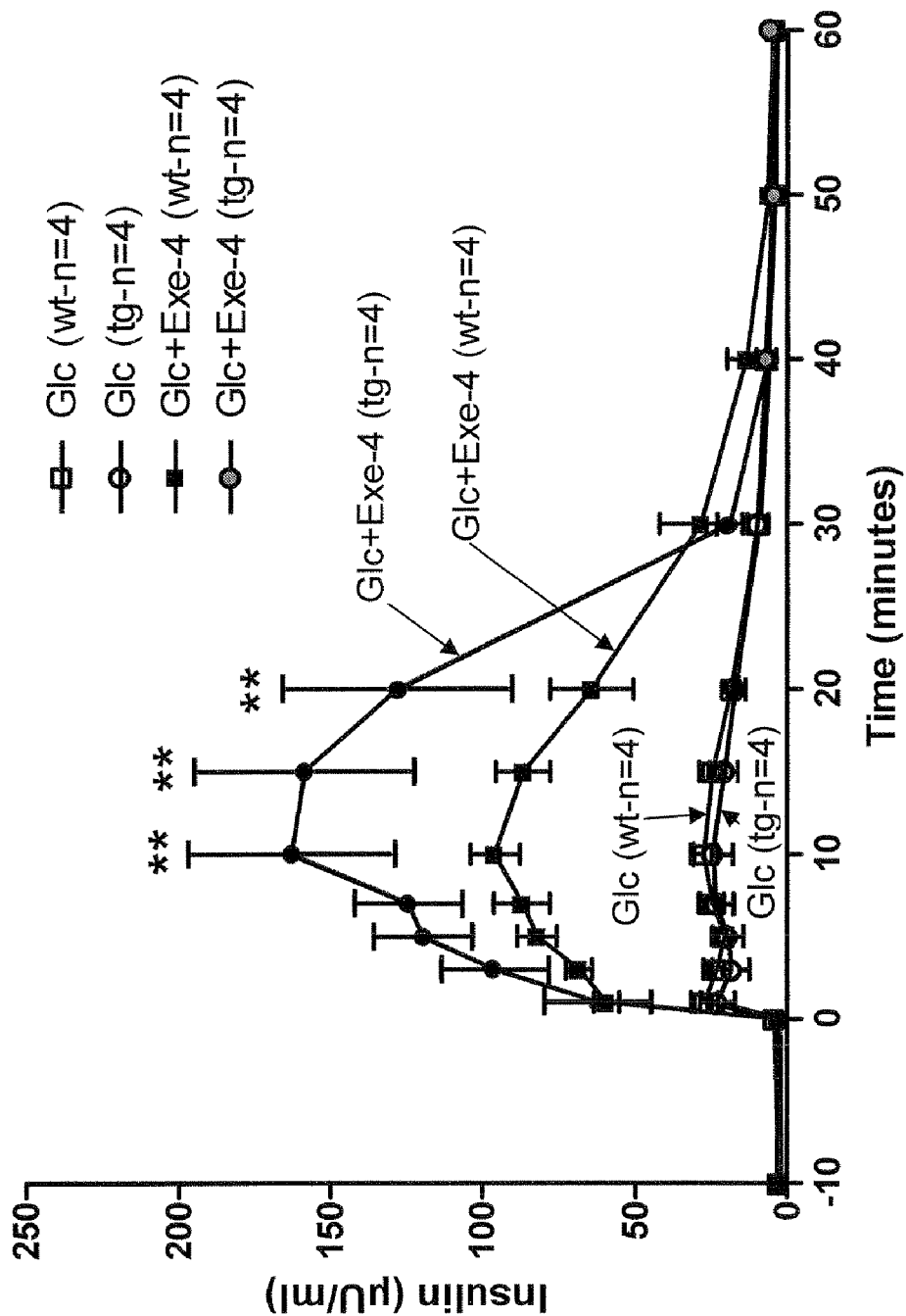

The potential of a preventive effect of incretin therapies is exemplified by an increased insulin secretion in response to the GLP-1 receptor agonist Exendin-4 in transgenic vs. control pigs (see e.g. FIG. 9b).

In a further preferred embodiment, a method for identifying targets to bypass or overcome a GIPR signaling defect is provided, comprising the utilization of a transgenic pig according to the present invention.

As described above, in an embodiment of the invention, promoters with other tissue specificities are used to evaluate the role of GIP receptor function in other GIP target tissues, such as adipose tissue, bone, and brain. These promoters can also be used in the methods of the invention, such as in order to identify compounds that modulate the incretin hormone system or complex in specific tissues or in a tissue-specific manner.

To evaluate the role of impaired GIP function in the pathogenesis of type 2 diabetes (T2D) in a clinically relevant animal model, the inventors generated transgenic pigs expressing a dominant-negative GIP receptor (GIPR dn) in the pancreatic islets using lentiviral transgenesis. Eleven-week-old GIPR$^{dn}$ transgenic pigs exhibited significantly reduced oral glucose tolerance with a delay in insulin secretion, whereas intravenous glucose tolerance and pancreatic β-cell mass were not different from controls. Also, the insulinotropic effect of intravenously administrated GIP was blunted ($p<0.05$), whereas the insulinotropic effect of the GLP-1 receptor agonist Exendin-4 was not only persevered but enhanced in GIPR$^{dn}$ pigs compared to controls ($p<0.01$).

At the age of 5 months, insulin secretion in response to oral glucose challenge was markedly ($p<0.01$) reduced in GIPR$^{dn}$ transgenic pigs, resulting in significantly elevated glucose levels ($p<0.05$). Importantly, pancreatic β-cell mass was reduced by almost 60% ($p<0.01$) in young adult GIPR$^{dn}$ transgenic pigs compared to controls.

These findings demonstrate that impaired GIP function is sufficient to cause reduced insulin secretion and a dramatic loss in β-cell mass. Treatment with Exendin-4, a potent GLP-1 receptor agonist used for therapy of T2D patients, resulted in a significant stimulation of insulin secretion in GIPR$^{dn}$ transgenic pigs. Taken together, the inventors generated the first large animal model for the analysis of incretin function that mimics important aspects of human T2D and has great potential for the evaluation of efficacy and safety of therapeutic strategies.

Preferred Embodiments of the Invention

The inventors generated a large animal model mimicking the impaired GIP function in T2D patients. A lentiviral vector was cloned that expresses a dominant-negative GIPR (GIPR$^{dn}$) under the control of the rat insulin 2 gene promoter (RIPII) (FIG. 1a). The GIPR$^{dn}$ has an eight amino acid deletion (positions 319-326) and an Ala→Glu exchange at amino acid position 340 in the third intracellular loop, which is essential for signal transduction (11).

Lentiviral vectors were injected into the perivitelline space of pig zygotes. A total of 113 injected zygotes were transferred laparoscopically into the oviducts of three cycle synchronized recipient gilts (sow 1: 32 zygotes; sow 2: 31 zygotes, sow 3: 50 zygotes) (12). 19 piglets (17% of the transferred zygotes) were born. Southern blot analysis identified 9 founder animals (47.3% of the born animals) carrying one or two lentiviral integrants (FIG. 1b), confirming the high efficiency of lentiviral transgenesis in large animals (12).

Figure 1B:
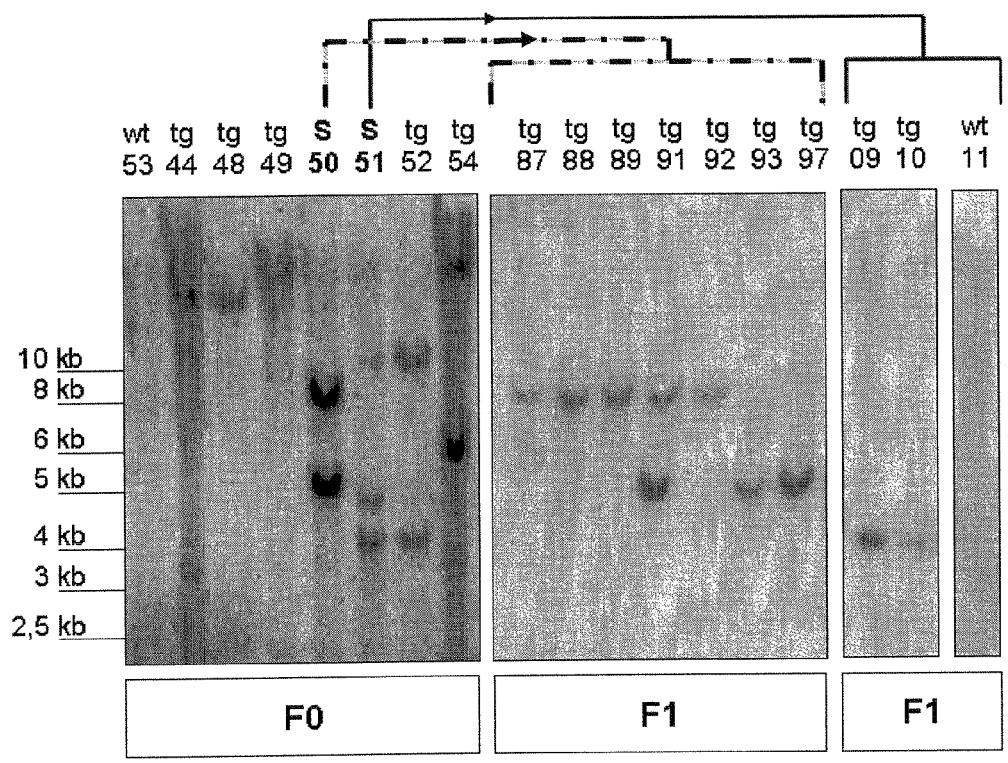

Two male founder animals (#50, #51) were mated to non-transgenic females (FIG. 1b). The resulting offspring demonstrated germ line transmission and segregation of the integrants according to mendelian rules (FIG. 1b).

Figure 1C:
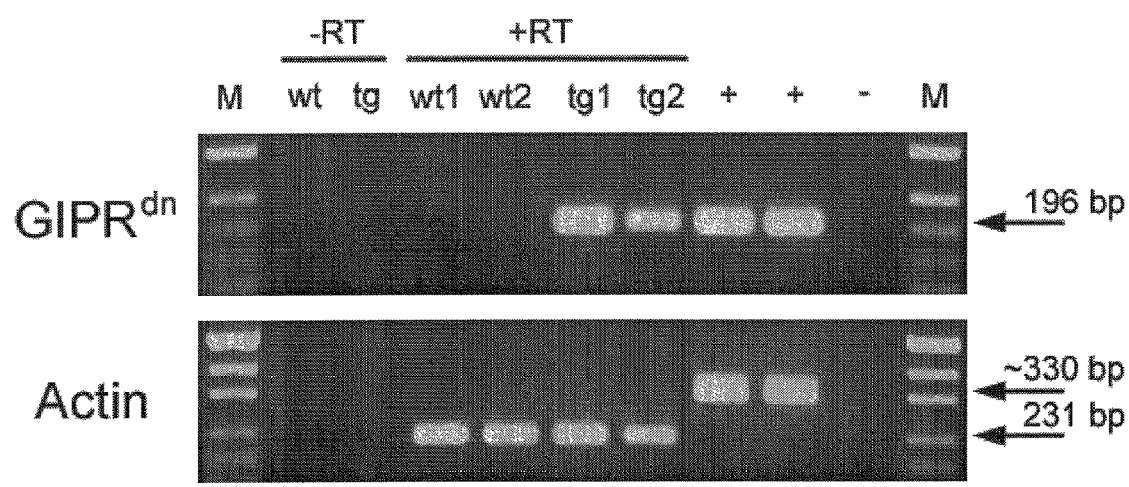

To analyze expression of GIPR$^{dn}$ mRNA, pancreatic islets were isolated from transgenic and non-transgenic offspring of both founder boars and analyzed by reverse transcriptase-polymerase chain reaction (RT-PCR). Expression of the GIPR$^{dn}$ was detected in the islets of all transgenic animals, but not in the islets of non-transgenic littermates. No signals were obtained from islets of transgenic offspring after omission of the RT step, demonstrating that expressed rather than integrated sequences were detected (FIG. 1c).

To evaluate effects of GIPR$^{dn}$ expression on glucose homeostasis, fasted blood glucose and serum fructosamine levels were determined in pigs from the age of one month up to the age of 7 months in regular intervals. No significant differences in blood glucose levels and serum fructosamine levels were detected between GIPR$^{dn}$ transgenic pigs and their non-transgenic control animals at any point of time investigated (data not shown). Random determination of fasting blood glucose levels up to an age of two years showed normoglycemia in GIPR$^{dn}$ transgenic pigs (data not shown).

An oral glucose tolerance test (2 g/kg body weight) was performed in 5-month-old (20±1 weeks) GIPR$^{dn}$ transgenic pigs (n=5) and littermate controls (n=5) originating from founder boars #50 and #51. GIPR$^{dn}$ transgenic pigs exhibited elevated glucose levels (FIG. 2a) as well as a distinct reduction of initial insulin secretion compared to their non-transgenic littermate controls (FIG. 2b). Also peak insulin levels were clearly reduced compared to controls. The area under the curve (AUC) for glucose was 26% (p<0.05) larger (FIG. 2a), whereas AUC for insulin was 49% (p<0.01) smaller in GIPR$^{dn}$ transgenic pigs (FIG. 2b). Reduced oral glucose tolerance in GIPR$^{dn}$ transgenic pigs is consistent with previous observations in mice lacking a functional GIPR (13). However, the latter model (13) did not exhibit structural changes of the pancreatic islets (see below).

Figure 3B:
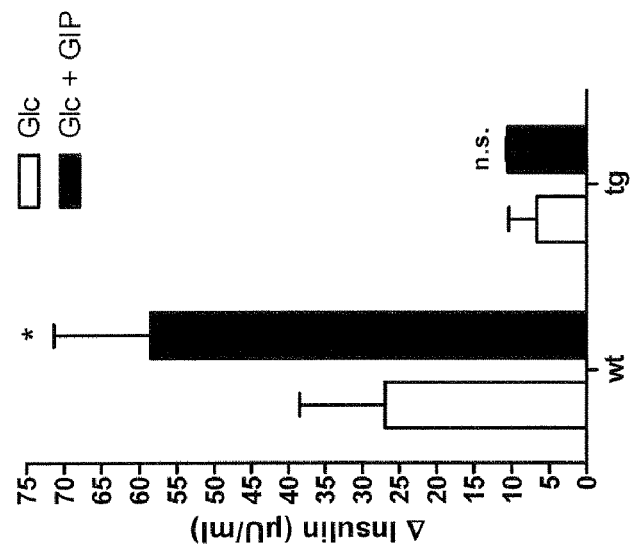
Figure 3A:
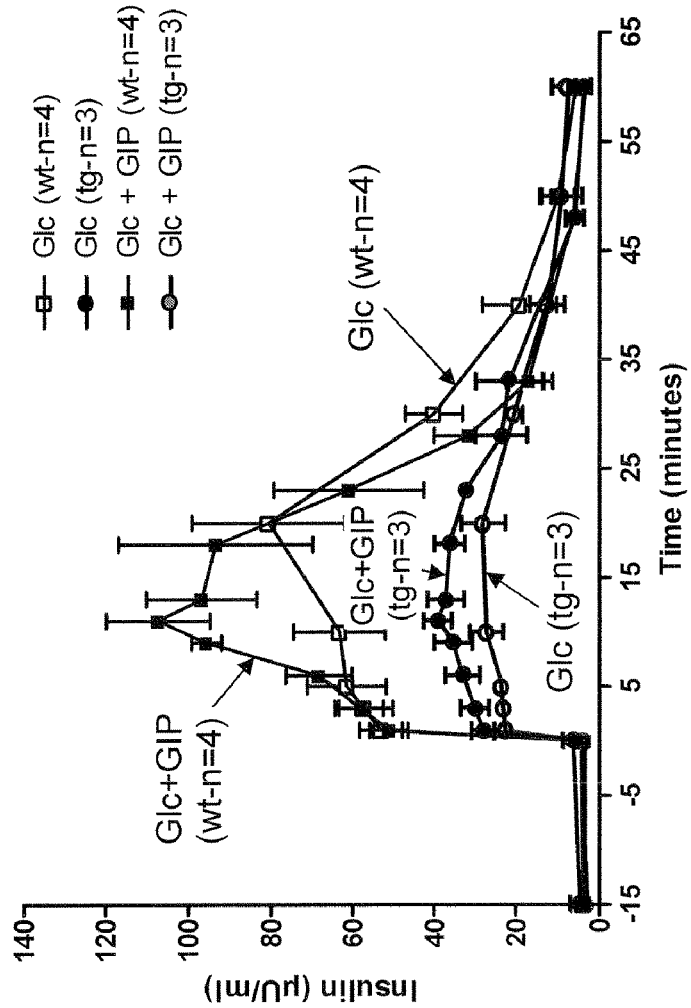

In order to further characterize the effect of GIPR$^{dn}$ expression, the inventors analyzed the effect of GIP in 28- to 36-week-old GIPR$^{dn}$ transgenic and control pigs (FIG. 3a). Intravenous (i.v.) injection of synthetic porcine GIP into control pigs resulted in a significant (p<0.05) increase in i.v. glucose-induced serum insulin concentration (58 µU/ml) as compared to the untreated controls (27 µU/ml) (FIG. 3b). In contrast, GIP administration induced only a small increase in glucose-induced insulin concentration (11 µU/ml) in GIPR$^{dn}$ transgenic pigs. In the untreated GIPR$^{dn}$ pigs glucose injection resulted in an insulin response that amounted to 7 µU/ml (FIG. 3b).

Figure 3D:
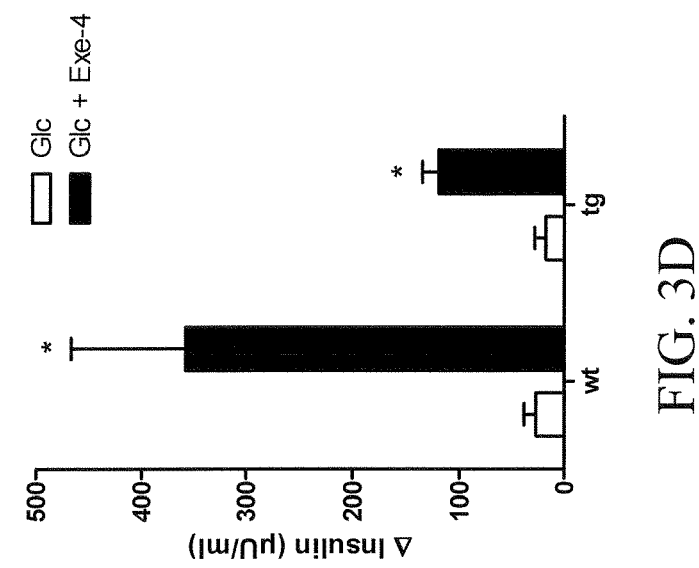
Figure 3C:
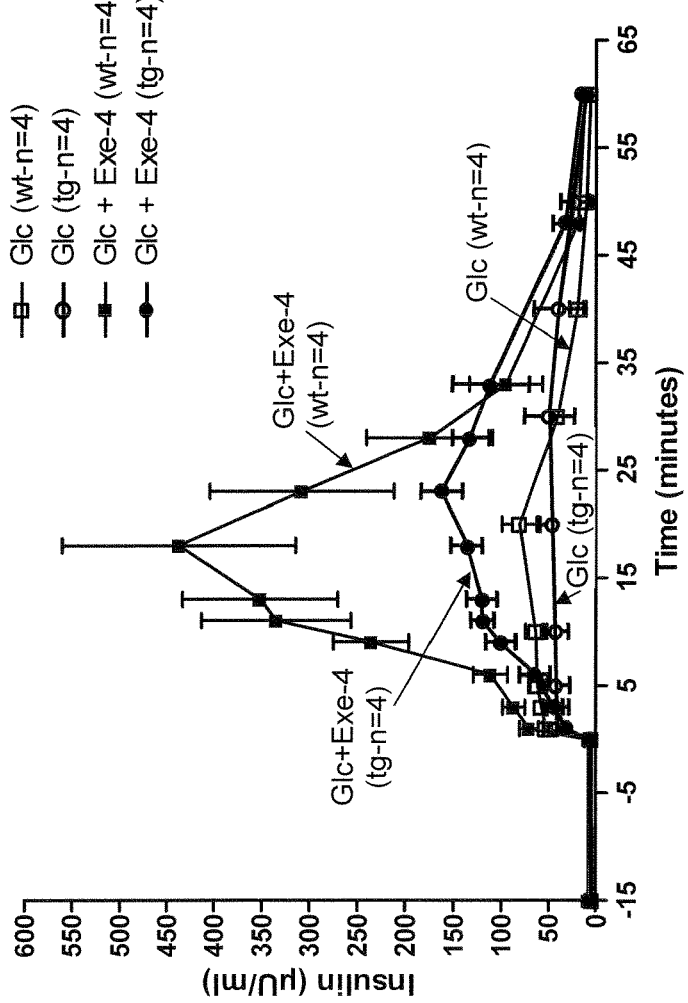

Next, the inventors tested the effect of Exendin-4, a naturally occurring, potent GLP-1 receptor agonist (4) (FIG. 3c). Application of Exendin-4 induced a significant increase of insulin secretion in GIPR$^{dn}$ transgenic pigs as well as in controls compared to glucose administration alone (p<0.05) (FIG. 3d). In both assays, GIPR$^{dn}$ transgenic pigs reached lower insulin levels following glucose and glucose+GIP/Exendin-4 administration than control animals (FIGS. 3a and c), suggesting a reduced insulin secretion capacity in GIPR$^{dn}$ transgenic pigs as compared to controls.

However, here two effects overlapped, namely the impaired incretin effect due to the expression of the GIPR$^{dn}$ and reduced insulin secretion capacity most likely due to an already reduced islet/β-cell mass at this age. A precision of these results was achieved in 10- to 13-week-old GIPR$^{dn}$ transgenic pigs compared to control pigs as β-cell mass is still unaltered at this age (see below).

An intravenous glucose tolerance test in 11-month-old (45 weeks±2 weeks) GIPR$^{dn}$ transgenic pigs (n=5) and littermate controls (n=4) revealed that GIPR$^{dn}$ transgenic pigs exhibited a significantly reduced insulin release (52% smaller AUC insulin; p<0.05) going along with a decelerated decline of blood glucose levels (10% larger AUC glucose; p<0.05) (FIG. 4). This observation strongly suggested that impaired GIPR function causes a general disturbance of insulin secretion and/or alterations in islet structure and/or islet integrity.

Markedly Reduced Pancreatic β-Cell Mass in Young Adult GIPR$^{dn}$ Transgenic Pigs.

To clarify this point, the inventors performed quantitative islet isolation experiments as well as quantitative stereological analyses of pancreata from young adult (1- to 1.4-year-old) GIPR$^{dn}$ transgenic pigs and controls. Pancreas weight did not differ between GIPR$^{dn}$ transgenic pigs and control animals (see Table 1). The organs were divided into two portions along a clearly defined anatomical structure (see FIG. 5). The left pancreatic lobe was processed for islet isolation (14). The number of isolated islet equivalents was reduced by 93% (p<0.05) in pancreas samples of GIPR$^{dn}$ transgenic pigs (n=3) as compared to littermate controls (n=3; Table 2).

TABLE 1

Weight of the total pancreas/pancreas portion of GIPR$^{dn}$ transgenic pigs (tg) and non-transgenic littermate control animals (wt) used for quantitative stereological analyses

| Type of Pig | Total pancreas weight[a] (gram) | Pancreas weight wo. left lobe[b] (gram) |
|---|---|---|
| wt #1 | 30 | 114 |
| wt #2 | 34 | 80 |
| wt #3 | 32 | 100 |
| wt #4 | 25 | 80 |
| wt #5 | 52 | 107 |
| mean ± SEM | 35 ± 5 | 96 ± 7 |
| tg #1 | 27 | 93 |
| tg #2 | 29 | 97 |
| tg #3 | 34 | 107 |
| tg #4 | 45 | 112 |
| tg #5 | 28 | 110 |
| mean ± SEM | 33 ± 3 | 104 ± 4 |

[a]11-week-old pigs;
[b]1-1.4-year-old pigs

TABLE 2

Results of islet isolation from pancreata of GIPR$^{dn}$ transgenic pigs (tg) and non-transgenic control animals (wt) (n = 3 in each group).

| Type of Pig | Total IEQ Purified | Total IEQ/ g Organ | Islet Purity (%)* | Islet Vitality (%)* |
|---|---|---|---|---|
| wt #1 | 72,673 | 889.71 | 95 | 95 |
| wt #2 | 90,260 | 1519.53 | 85 | 80 |
| wt #3 | 71,658 | 1119.66 | 85 | 80 |
| mean ± SEM | 78,197 ± 6,038 | 1176.23 ± 184 | 88.3 ± 3.33 | 85 ± 5.0 |
| tg #1 | 4,053 | 50.66 | 85 | 80 |
| tg #2 | 6,026 | 81.76 | 85 | 80 |
| tg #3 | 6,240 | 89.14 | 85 | 80 |
| mean ± SEM | 5,439 ± 696 | 73.85 ± 11.79 | 85 | 80 |

IEQ islet equivalent (islet of 150 µm size);
*estimation by two independent individuals after microscopic inspection.

Figure 6A:
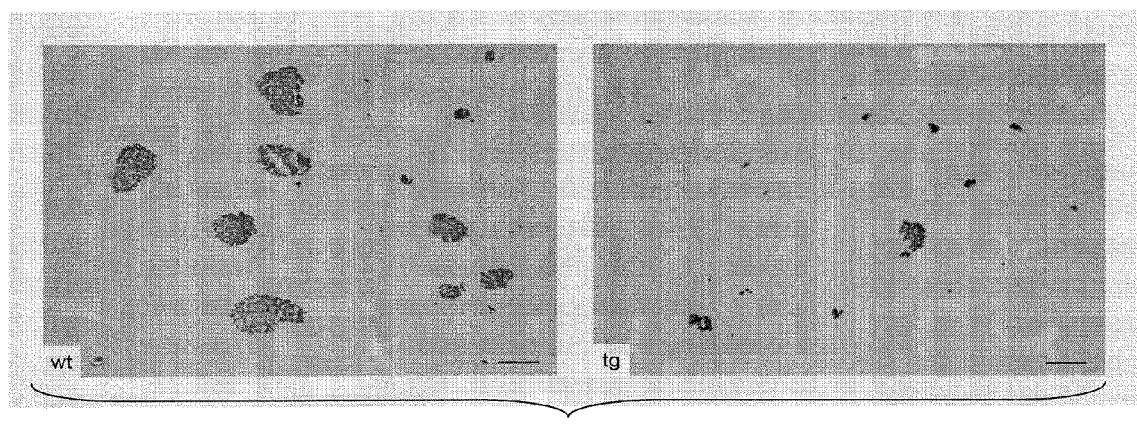
Figure 6B:
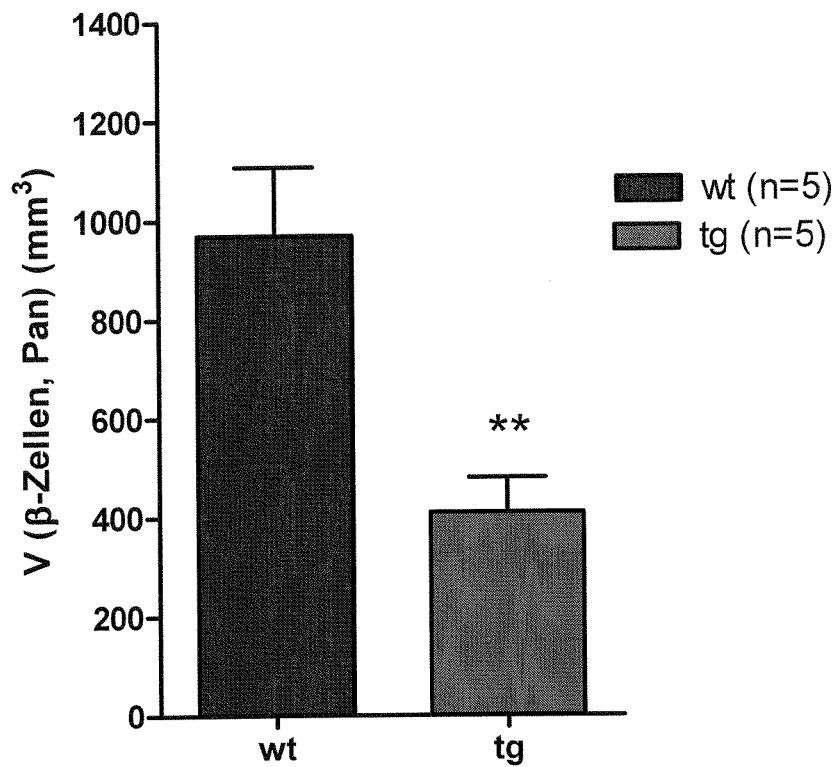
Figure 6C:
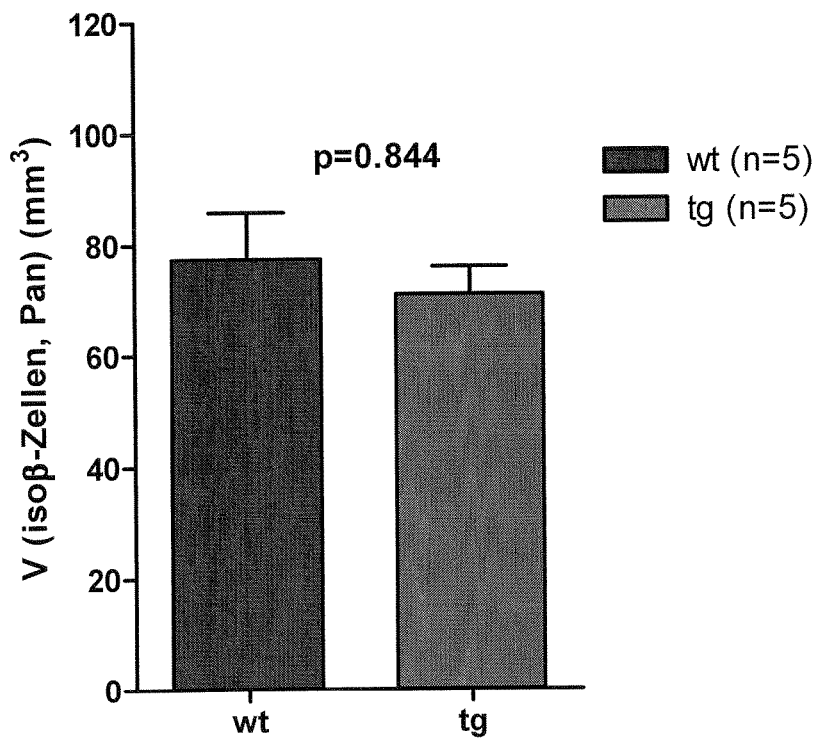

Qualitative histological assessment revealed that pancreatic islet profiles of GIPR$^{dn}$ transgenic pigs appeared to be smaller in size and reduced in number (FIG. 6a). These findings were confirmed by quantitative stereological investigations (15). The volume density of β-cells in the pancreas ($Vv_{(\beta\text{-cell}/Pan)}$) was markedly reduced by 61% (p<0.01) in GIPR$^{dn}$ transgenic pigs (n=5) vs. controls (n=5; data not shown). Accordingly, the total volume of β-cells ($V_{(\beta\text{-cell},Pan)}$; FIG. 6b) was significantly reduced (by 58%; p<0.01) in GIPR$^{dn}$ transgenic pigs compared to non-transgenic controls.

In contrast, volume density (data not shown) as well as the total volume (FIG. 6c) of isolated β-cells ($Vv_{(isoβ\text{-}cell/Pan)}$, $V_{(isoβ\text{-}cell,Pan)}$) were not different between the two groups. These data demonstrate a marked reduction of pancreatic β-cell mass in GIPR$^{dn}$ transgenic pigs, which is in line with previous evidence for a trophic action of GIP on β-cells in vitro (5-7).

Staining studies with an antibody that recognizes proliferating cells (anti-Ki67 antibody) revealed that the reduced pancreatic islet/β-cell mass in GIPR$^{dn}$ transgenic pigs is—at least in part—due to reduced cell proliferation (FIG. 10).

Disturbed Incretin Function in Young GIPR$^{dn}$ Transgenic Pigs.

Figure 7A:
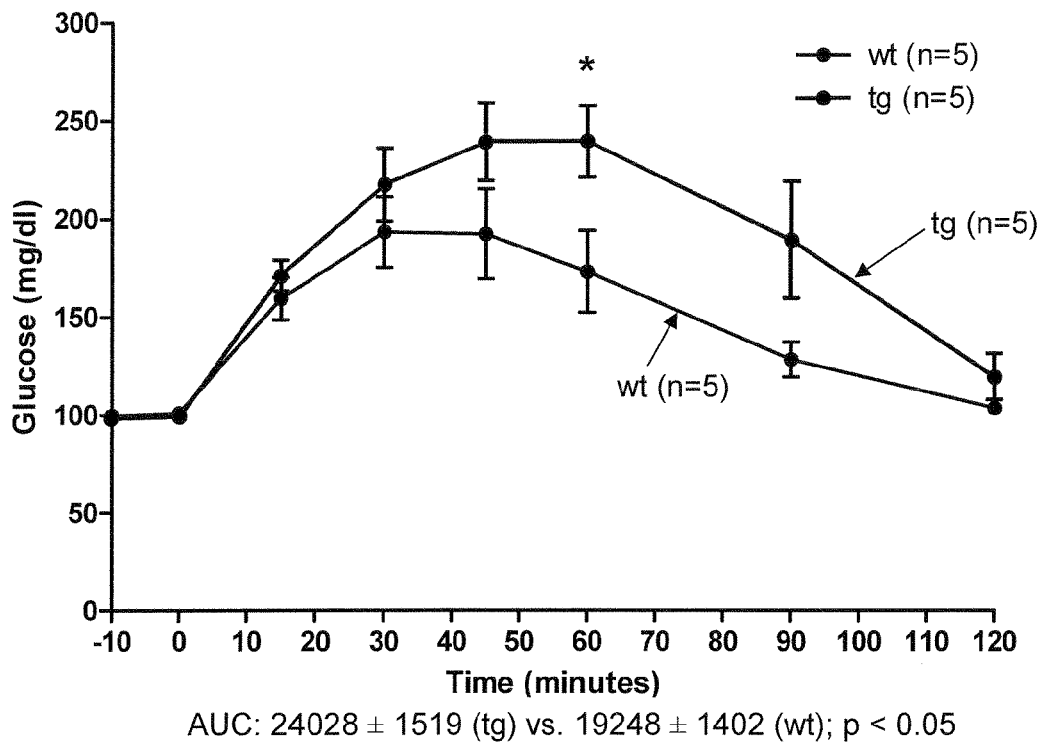
Figure 7B:
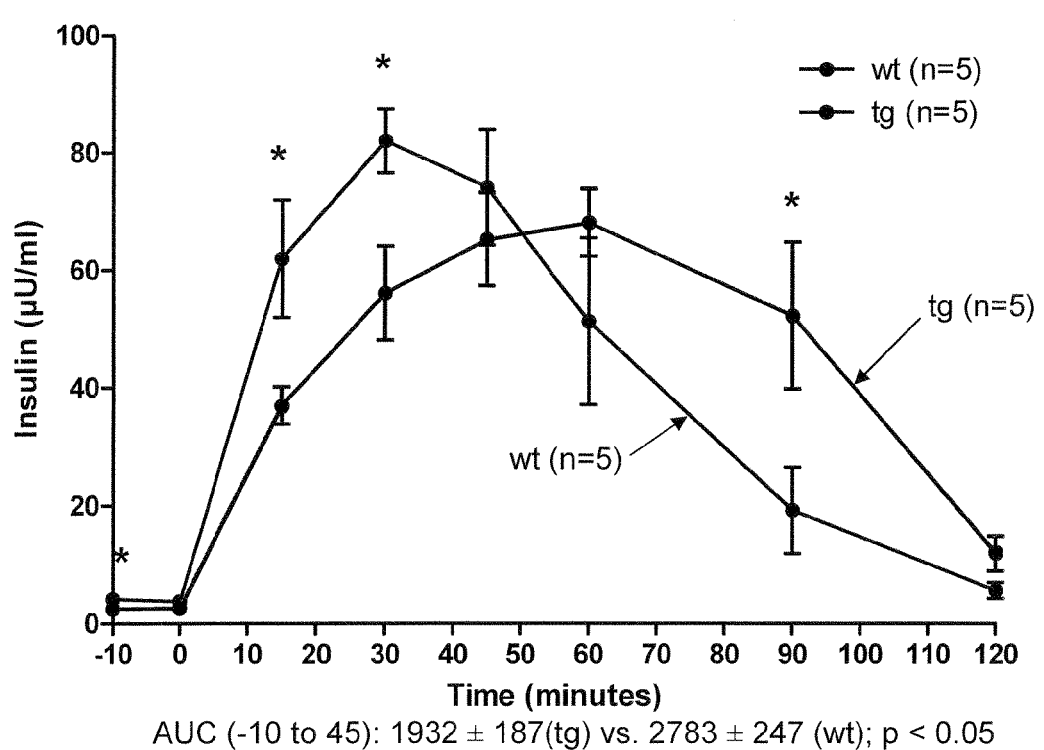
Figure 7C:
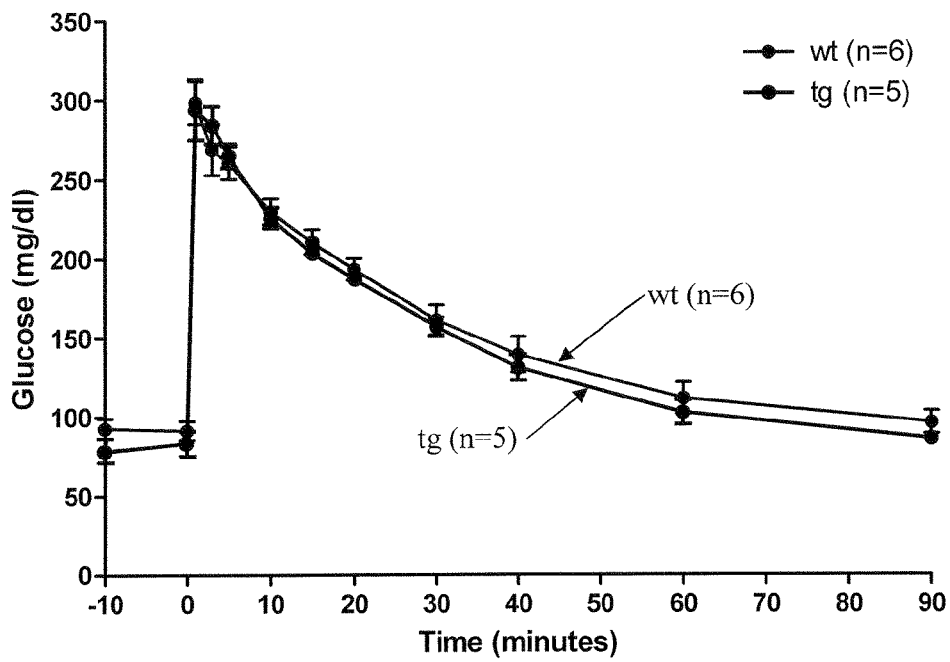
Figure 7D:
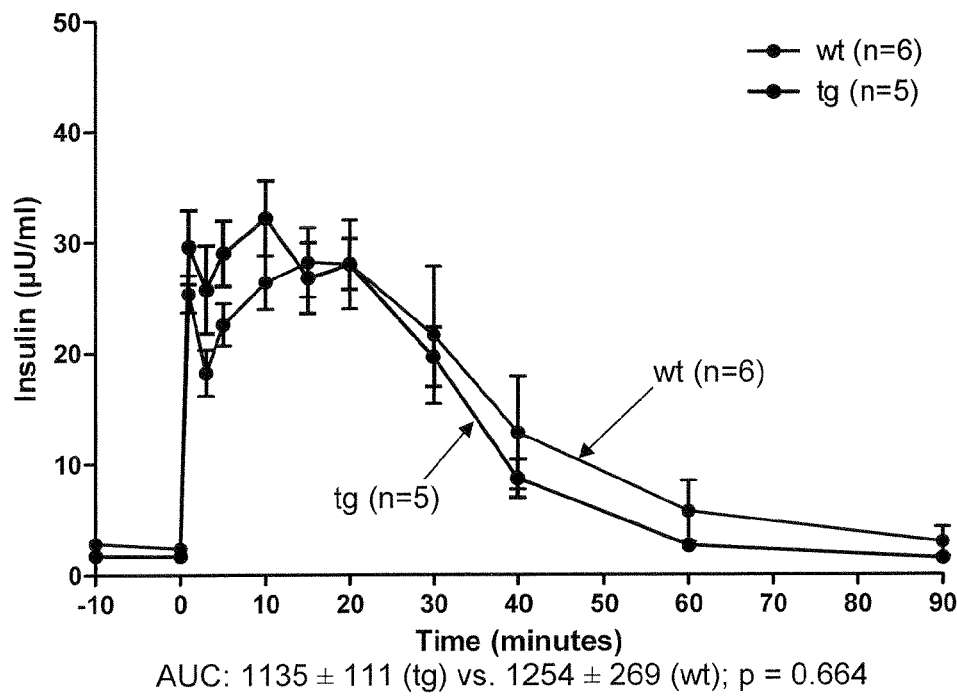
Figure 8B:
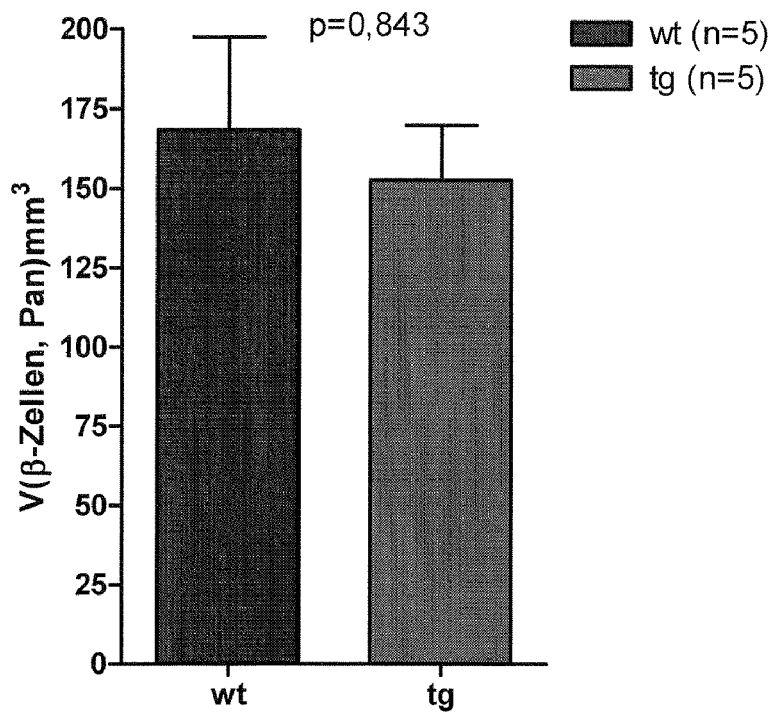
Figure 8C:
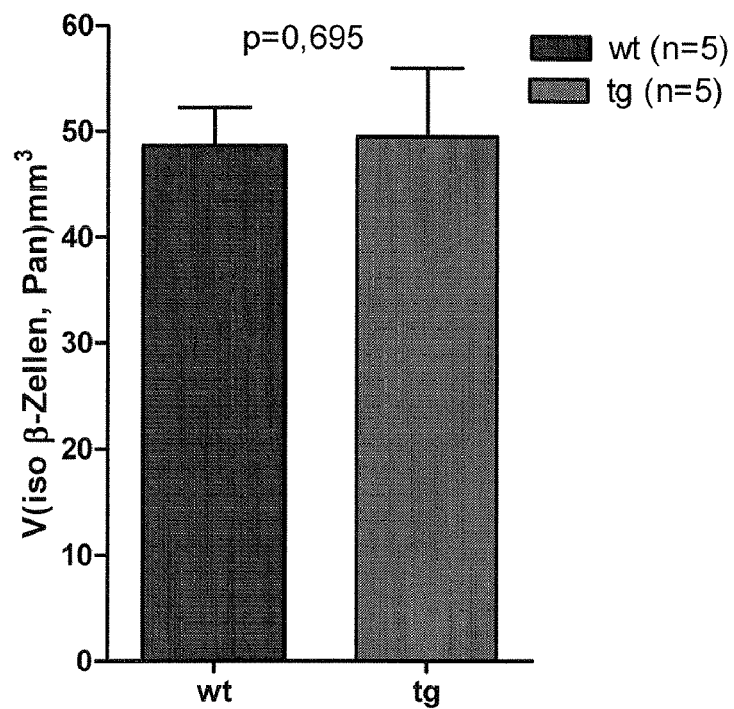

Furthermore, an oral glucose tolerance test (2 g glucose/kg body weight) was performed in 11-week-old GIPR$^{dn}$ transgenic pigs (n=5) and littermate controls (n=5) originating from founder boars #50 and #51. GIPR$^{dn}$ transgenic pigs exhibited elevated (p<0.05) serum glucose levels (FIG. 7a) as well as a distinct delay in insulin secretion (FIG. 7b) after glucose challenge. The area under the insulin curve (AUC) during the first 45 minutes following glucose challenge was 31% (p<0.05) smaller in GIPR$^{dn}$ transgenic pigs than in age-matched controls (FIG. 7b), however, the total amount of insulin secreted during the experimental period (120 minutes) was not different between the two groups, indicated by a comparable area under the insulin curve between the two groups (data not shown). These findings indicate that in our pig model expression of a GIPR$^{dn}$ in the pancreatic islets is sufficient to interfere with the incretin effect, but does initially not affect the total insulin secretion capacity. This assumption is supported by the fact that intravenous glucose tolerance was not reduced in GIPR$^{dn}$ transgenic pigs (FIG. 7c) and the time course and amount of insulin secreted in response to an intravenous glucose load were not different between the two groups (FIG. 7d). Quantitative stereological investigations of the pancreas (15) revealed that the total volume of β-cells in the pancreas was not different between GIPR transgenic pigs and controls (202±50 mm$^3$ vs. 218±67 mm$^3$; p=0.843; FIG. 8b). Further, the total volume of isolated β-cells (single insulin positive cells and small clusters of insulin positive cells not belonging to established islets), a parameter indicative of islet neogenesis, was similar in the two groups (49±14 mm$^3$ vs. 49±8 mm$^3$; p=0.695; FIG. 8c). In summary, these findings clearly demonstrate that expression of a GIPR$^{dn}$ initially neither interferes with pancreatic islet development/maintenance nor exhibits a toxic effect on pancreatic islets.

Impaired Insulinotropic Effect of GIP, but Enhanced Insulinotropic Effect of Exendin-4 in GIPR$^{dn}$ Transgenic Pigs.

In order to proof the specificity of GIPR$^{dn}$ expression, the inventors analyzed the effect of GIP and Exendin-4 in 10- to 13-week-old GIPR$^{dn}$ transgenic and control pigs (FIG. 9a/b). Intravenous (i.v.) injection of synthetic porcine GIP together with glucose into control pigs resulted in significantly (p<0.01) higher insulin levels compared to GIPR$^{dn}$ transgenic pigs (FIG. 9a/c). In contrast, application of Exendin-4, a naturally occurring, potent GLP-1 receptor agonist (4) together with glucose induced a significantly higher increase of insulin secretion in GIPR transgenic pigs compared to controls (p<0.01) (FIG. 9b/c). Thus, the effects of GIP are reduced in GIPR$^{dn}$ transgenic pigs, mirroring the situation in human T2D patients. In contrast, the effects of GLP-1/GLP-1 mimetics are enhanced compared to controls which points to a compensatory mechanism of the GLP-1/GLP-1R axis for the reduction of GIP function.

This study established for the first time a transgenic large animal model of impaired incretin function. Given the high physiologic and metabolic similarities between humans and pigs, porcine models of diabetic disease are more relevant than rodent models.

GIPR knockout mice (Gipr$^{-/-}$) provided no evidence that GIPR action is required for the maintenance of islet and β-cell integrity in vivo (16,17) Interestingly, these mice exhibited an increase in relative β-cell area referring to pancreas area (16), leading to the conclusion that in vivo the function of GIP is primarily restricted to that of an incretin (17). The relatively mild phenotype of Gipr$^{-/-}$ mice may result from compensatory mechanisms (17). Islets from Gipr$^{-/-}$ mice were shown to exhibit increased sensitivity to exogenous GLP-1 (16). Although double mutant mice (DIRKO) lacking both GIPR and GLP-1R exhibited more severe glucose intolerance than the individual mutants (18,19), also these double mutant animals did not develop diabetes mellitus.

In contrast, RIPII-GIPR$^{dn}$ transgenic mice develop massive early-onset diabetes mellitus with marked structural changes of the pancreatic islets (11), precluding long-term studies as to the role of GIP signaling for islet maintenance in the absence of glucose toxicity. The massive changes observed in GIPR$^{dn}$ transgenic mice were unexpected and are possibly due to a high level of overexpression of the dominant-negative receptor which may cause—in part—non-specific effects, e.g. by squelching of G-proteins. This assumption is supported by the fact, that GIPR$^{dn}$ transgenic mice do not respond with a significant increase in insulin secretion to either GIP or GLP-1 (11).

The analysis of the GIPR$^{dn}$ transgenic pigs suggests that—apart from its role as an incretin hormone—GIP is necessary for the survival of β-cells in large mammals. The findings of the inventors further support the notion that reduced responsiveness to GIP might be an early step in the pathogenesis of T2D (10).

In conclusion, GIPR$^{dn}$ transgenic pigs represent a more clinically relevant animal model for a plethora of applications in basic and translational research including the detailed characterization of mechanisms by which GIP supports islet maintenance in vivo, the development and preclinical evaluation of incretin-based therapies (reviewed in 20) as well as the development of novel methods for dynamic monitoring of islet mass in T2D patients (21).

The following examples illustrate the present invention without, however, limiting the same thereto.

EXAMPLES

Example 1

Lentiviral Constructs

The expression cassette consisting of the rat insulin 2 promoter (RIPII) and the cDNA of a dominant-negative human glucose-dependent insulinotropic polypeptide receptor (GIPR$^{dn}$) was described previously (11) and cloned into the lentiviral vector LV-pGFP (22) via the ClaI and SalI restriction sites. Recombinant lentivirus was produced as previously described (22).

The respective cDNA sequence is shown in SEQ ID NO: 2. The respective amino acid sequence is shown in SEQ ID NO: 1.

Example 2

Generation of Transgenic Animals

Zygotes were collected from 6-month old superovulated and artificially inseminated gilts after slaughter as previously described (12). As recipients six-month-old estrus-synchronized gilts were used. Pig embryo transfers were performed laparoscopically as previously described (23).

Briefly, gilts, 6-7 months of age, were used as zygote donors. Superovulation was performed by an intramuscular injection of 1200 IU of pregnant mare serum gonadotropin (PMSG) (Intergonan®, Intervet, Unterschleissheim, Germany) and 72 hours later ovulation was stimulated by an intramuscular injection of 750 IU of human chorionic gonadotropin (hCG) (Ovogest®, Intervet). 24 and 36 hours after hCG injection, donors were artificially inseminated with $3 \times 10^9$ sperms of a German Landrace boar suspended in 100 ml of a commercial BTS extender (Beltsville). 32 to 34 hours after the first insemination, donor gilts were slaughtered and genital tracts were collected. After transport to the laboratory in a 37° C. temperated box (Labotec thermo-cell-transporter, Labotec, Bovenden-Göttingen, Germany), corpora lutea were counted and oviducts were flushed into a polystyrene culture dish (d 10 cm, Nunclon, Roskilde, Denmark). The flushing medium consisted of PBS supplemented with 20% heat-inactivated lamb serum (Gibco, BRL) and 50 mg/L gentamicin sulphate (Sigma-Aldrich, Taufkirchen, Germany). Zygotes were collected followed by subzonal virus injection into the perivitelline space using glass capillaries under an inverted microscope (Axiovert 135, Zeiss). Embryo transfer was performed the same day.

As recipients six-month-old estrus-synchronized gilts were used. Synchronization by oral administration of altrenogest (Regumate®, Serumwerk Bernburg, Bernburg, Germany) over a 15-day period was followed by administration of 750 IU PMSG. Ovulation was induced 72 hours later with 750 IU hCG. Embryo transfers were performed laparoscopically under general anesthesia with a combination of 2 ml per 10 kg body weight (BW) ketamine hydrochloride (Ursotamin®, Serumwerk Bernburg) and 0.5 ml per 10 kg xylazine (Xylazin 2%, WDT, Germany) injected intravenously. Thirty-50 injected embryos were transferred in one oviduct of each recipient.

Animals investigated in this study were hemizygous male and female transgenic pigs and non-transgenic (littermate) control animals. Animals were trained carefully in all experimental procedures before the start of experiments. All animal experiments were carried out according to the German Animal Protection Law.

Example 3

Genotyping

Offspring were genotyped by PCR using DNA prepared from ear tips by application of the Wizard DNA Extraction Kit (Clontech, Mountain View, USA). Transgene-specific primers were used:

```
sense:
5'-TTT TTA TCC GCA TTC TTA CAC GG-3' [SEQ ID NO: 3]
and antisense
5'-ATC TTC CTC AGC TCC TTC GAG G-3'. [SEQ ID NO: 4]
```

For Southern blot analysis, genomic DNA (aliquots of 8 μg) extracted from EDTA blood using the Blood and Cell Culture DNA Midi kit (Qiagen, Hilden, Germany), was digested with the restriction enzyme ApaI and hybridized with a $^{32}$P-labeled probe directed towards the RIPII promoter sequence.

Example 4

Expression Analysis by RT-PCR

Total RNA was extracted using TRIzol® Reagent (Invitrogen, Karlsruhe, Germany) with Linear Acrylamide (Ambion, Foster City, USA) as a coprecipitant according to the manufacturer's instructions. 400 ng of total RNA were then reversibly transcribed into cDNA using SuperScriptII reverse transcriptase (Invitrogen, Karlsruhe, Germany) and random hexamer primers (Invitrogen) after performance of a DNase digest using DNaseI (Roche, Mannheim, Germany). For PCR, the following transgene specific primers were used:

```
sense:
5'-TTT TTA TCC GCA TTC TTA CAC GG-3' [SEQ ID NO: 3]
and antisense
5'-ATC TTC CTC AGC TCC TTC CAG G-3'. [SEQ ID NO: 4]
```

Example 5

Non-Surgical and Surgical Implantation of Central Venous Catheters

For the oral glucose tolerance test (OGTT), one central venous catheter (Cavafix® Certo®, B. Braun, Melsungen, Germany) was inserted non-surgically into the external jugular vein under general anesthesia according to the manufacturer's instructions. For accomplishment of the GIP/Exendin-4 stimulation test as well as the intravenous glucose tolerance test, two central venous catheters (Cavafix® Certo®, B. Braun) were surgically inserted into the external jugular vein under general anesthesia using a modified method of Moritz et al. (24). At the start of the study period, all animals had fully recovered from the surgical procedure as evaluated by normal behavior and food intake.

Example 6

Oral Glucose Tolerance Test (OGTT)

The OGTT was performed in 11-week old and 5-month-old non-restrained, freely moving animals. After an 18-h overnight fast, animals were fed 2 g/kg BW glucose (25) mixed with 100 g of commercial pig fodder (Deuka primo care in 11-week-old pigs; Deuka porfina U in 5-month-old pigs; Deuka, Düsseldorf, Germany). The meal was eaten from a bowl under supervision. Blood samples were obtained from the jugular vein catheter at −10, 0, 15, 30, 45, 60, 90 and 120 minutes relative to the glucose load in 11-week-old pigs and at −15, −5, 0, 15, 30, 45, 60, 90, 120, 150 and 180 minutes relative to the glucose load in 5-month-old pigs. Serum glucose levels were determined using an AU 400 autoanalyzer (Olympus, Hamburg, Germany) while serum insulin levels were measured in duplicate using a porcine insulin radioimmunoassay (RIA) kit (Millipore, Billerica, USA) according to the manufacturer's instructions.

Example 7

GIP/Exendin-4 Stimulation Test

The GIP/Exendin-4 stimulation test was performed in 10- to 13-week old and 7-months-old (28-36 weeks) non-restrained freely moving animals. In 7-months-old animals, 0.5 g glucose/kg BW were administered intravenously as a bolus of concentrated 50% glucose solution following an 18-hour fasting period (26). After three minutes 20 pmol/kg BW of synthetic porcine GIP (Bachem, Weil am Rhein, Germany) or 10 pmol/kg BW of synthetic Exendin-4 (Bachem) were administered intravenously. Blood samples were collected −15, 0, 1, 3, 6, 9, 11, 13, 18, 23, 28, 33, 48 and 60 minutes relative to the glucose load. In 10- to 13-week-old animals, 0.5 g glucose/kg BW were administered intravenously as a bolus of concentrated 50% glucose solution following an 18-hour fasting period (26). Right after glucose administration 80 pmol/kg BW of synthetic porcine GIP (Bachem, Weil am Rhein, Germany) or 40 pmol/kg BW of synthetic Exendin-4 (Bachem) were administered intravenously. Blood samples were collected −10, 0, 1, 3, 5, 7, 10, 15, 20, 30, 40, 50, and 60 minutes relative to the glucose load.

The day before the GIP stimulation test and two days before the Exendin-4 stimulation test, an intravenous glucose tolerance test (IVGTT) using 0.5 g/kg BW of 50% concentrated glucose solution was performed as described below (Example 8).

Example 8

Intravenous Glucose Tolerance Test (IVGTT)

The IVGTT was performed in 11-week-old pigs and in pigs at 11 months (45 weeks±2 weeks) of age. After an 18-h overnight fast, a bolus injection of concentrated 50% glucose solution (0.5 g glucose/kg BW) (26) was administered through the central venous catheter. Blood was collected at −10, 0, 1, 3, 5, 10, 20, 30, 40, 60 and 90 minutes relative to the glucose load in 11-week-old pigs and at −15, −5, 0, 1, 3, 5, 10, 20, 30, 40, 50, 60, 120 and 180 minutes relative to the glucose load in 11 month-old pigs. Serum glucose and serum insulin levels were determined as described above (Example 7).

Example 9

Pancreas Preparation and Islet Isolation

Pancreatic islets were isolated from three 12- to 13-month-old GIPR$^{dn}$ transgenic pigs and three littermate control animals (~220 kg). After precise explantation of the pancreata in toto, the major pancreatic duct was canulated using a Cavafix® Certo 18G catheter (B. Braun). Following separation from the rest of the organ along a clearly defined anatomical structure (see FIG. 5), the left pancreatic lobe was distended with University of Wisconsin (UW) solution containing 4 PZ units NB8 collagenase (Nordmark, Uetersen, Germany) per gram of organ and 0.7 DMC units neutral protease (Nordmark). The pancreata were digested using a modification of the half-automated digestion-filtration method as previously described (27). Purification of the isolated islets was performed with the discontinuous OptiPrep™ density gradient (Progen, Heidelberg, Germany) in the COBE 2991 cell processor (COBE Inc., Colorado, USA) (28). Purified islets were cultured in HAM'S F12 culture medium (Cell Concepts, Umkirch, Germany; supplemented with 10% FCS, 1% amphotericine B, 1% L-glutamine, 1% ampicilline/gentamycine and 50 mM nicotinamide) at 24° C. and 5% $CO_2$ in air. Islet numbers were determined using dithizone (DTZ) stained islet samples (29) (triplicates) which were counted under an Axiovert 25 microscope (Zeiss, Oberkochen, Germany) with a calibrated grid in the eyepiece, grouped into size categories and converted into islet equivalents (IEQ), i.e., islets with an average diameter of 150 μm. Purity of the islets was estimated by two independent individuals using dithizone stained samples of the islet suspension (triplicates). For determination of islet vitality, an aliquot of the islet suspension was stained with freshly prepared fluorescein diacetate (FDA, Sigma) and propidium iodide solution (PI, Sigma) and then estimated by two independent individuals using a BX50 fluorescence microscope (Olympus).

Example 10

Quantitative Stereological Analyses

Quantitative stereological analyses were carried out in 1-1.4-year-old animals using the pancreas without the left pancreatic lobe (separation of the left pancreatic lobe from the rest of the organ described above, Example 9) and in 11-week-old animals using the whole pancreas.

Following prefixation, the pancreas was cut into 1 cm thick slices. Slices were tilted to their left side and covered by a 1 $cm^2$ point-counting grid. For quantitative-stereological analyses, tissue blocks were selected by systematic random sampling, fixed in 10% neutral buffered formalin, routinely processed and embedded in paraffin. From a series of approximately 4 μm thick sections, one section was stained with hematoxylin and eosin (H&E) and the following two sections were used for immunohistochemistry. The volume of the pancreas ($V_{(Pan)}$) before embedding was calculated by the quotient of the pancreas weight and the specific weight of the pig pancreas (1.07 g/$cm^3$). The specific weight was determined by the submersion method (30). The volume density of β-cells in the pancreas ($Vv_{(\beta\text{-}cell/Pan)}$), the total volume of β-cells in the pancreas ($V_{(\beta\text{-}cell,\ Pan)}$, the volume density of isolated β-cells in the pancreas ($Vv_{(iso\ \beta\text{-}cell/Pan)}$) and the total volume of isolated β-cells in the pancreas ($V_{(iso\ \beta\text{-}cell,\ Pan)}$) were determined as described previously (15).

Cell proliferation index was defined as the number of immunolabelled (Ki67 positive) cell nuclei divided by the number of cell nuclei counted, and expressed as the number of immunolabelled (Ki67 positive) cell nuclei/$10^5$ cell nuclei.

Example 11

Immunohistochemistry

The indirect immunoperoxidase technique was applied to localize insulin containing cells as previously described (11). A polyclonal guinea pig anti-porcine insulin antibody (dilution 1:1,000) (Dako Cytomation, Hamburg, Germany) as well as horseradish peroxidase conjugated polyclonal rabbit anti-guinea pig IgG (dilution 1:50 containing 5% (vol/vol) porcine serum) were used.

To localize Ki67 containing nuclei a monoclonal mouse anti-human Ki67 antibody (dilution 1:8) (Dako Cytomation, Hamburg, Germany) as well as a biotinylated polyclonal goat anti-mouse antibody (dilution 1:200 containing 5% (vol/vol) porcine serum) were used.

Example 12

Statistics

All data are presented as means±SEM. Statistical significance of differences between groups (GIPR$^{dn}$ transgenic vs. control) was tested using the Mann-Whitney-U-Test in combination with an exact test procedure. Data from the GIP/Exendin-4 stimulation tests (Δ insulin) in 7-months-old (28-

36 weeks) animals were transformed to natural logarithms (ln) to approximate Gaussian distribution and subsequently compared by using a paired t-test (SPSS 16.0). Data from the GIP/Exendin-4 stimulation tests in 10- to 13-week-old animals as well as from proliferation index (Ki67 immunohistochemistry) were analyzed using ANOVA (analysis of variance) (SAS). P values less than 0.05 were considered significant.

The features disclosed in the foregoing description, in the claims and/or in the accompanying drawings may, both separately and in any combination thereof, be material for realizing the invention in diverse forms thereof.

REFERENCES

1. Nauck, M. A. et al. Preserved incretin activity of glucagon-like peptide 1 [7-36 amide] but not of synthetic human gastric inhibitory polypeptide in patients with type-2 diabetes mellitus. *J. Clin. Invest* 91, 301-307 (1993).
2. Baggio, L. L. & Drucker, D. J. Biology of incretins: GLP-1 and GIP. *Gastroenterology* 132, 2131-2157 (2007).
3. Mayo, K. E. et al. International Union of Pharmacology. XXXV. The glucagon receptor family. *Pharmacol. Rev.* 55, 167-194 (2003).
4. Holst, J. J. & Gromada, J. Role of incretin hormones in the regulation of insulin secretion in diabetic and nondiabetic humans. *Am. J. Physiol Endocrinol. Metab* 287, E199-E206 (2004).
5. Trumper, A. et al. Glucose-dependent insulinotropic polypeptide is a growth factor for beta (INS-1) cells by pleiotropic signaling. *Mol. Endocrinol.* 15, 1559-1570 (2001).
6. Trumper, A., Trumper, K. & Horsch, D. Mechanisms of mitogenic and anti-apoptotic signaling by glucose-dependent insulinotropic polypeptide in beta(INS-1)-cells. *J. Endocrinol.* 174, 233-246 (2002).
7. Ehses, J. A. et al. Glucose-dependent insulinotropic polypeptide promotes beta-(INS-1) cell survival via cyclic adenosine monophosphate-mediated caspase-3 inhibition and regulation of p38 mitogen-activated protein kinase. *Endocrinology* 144, 4433-4445 (2003).
8. Kim, S. J. et al. Glucose-dependent insulinotropic polypeptide (GIP) stimulation of pancreatic beta-cell survival is dependent upon phosphatidylinositol 3-kinase (PI3K)/protein kinase B (PKB) signaling, inactivation of the forkhead transcription factor Foxo1, and down-regulation of bax expression. *J. Biol. Chem.* 280, 22297-22307 (2005).
9. Yusta, B. et al. GLP-1 receptor activation improves beta cell function and survival following induction of endoplasmic reticulum stress. *Cell Metab* 4, 391-406 (2006).
10. Nauck, M. A., Baller, B. & Meier, J. J. Gastric inhibitory polypeptide and glucagon-like peptide-1 in the pathogenesis of type 2 diabetes. *Diabetes* 53 Suppl 3, S190-S196 (2004).
11. Herbach, N. et al. Overexpression of a dominant negative GIP receptor in transgenic mice results in disturbed postnatal pancreatic islet and beta-cell development. *Regul. Pept.* 125, 103-117 (2005).
12. Hofmann, A. et al. Efficient transgenesis in farm animals by lentiviral vectors. *EMBO Rep.* 4, 1054-1060 (2003).
13. Miyawaki, K. et al. Glucose intolerance caused by a defect in the entero-insular axis: a study in gastric inhibitory polypeptide receptor knockout mice. *Proc. Natl. Acad. Sci. U. S. A* 96, 14843-14847 (1999).
14. Krickhahn, M., Meyer, T., Buhler, C., Thiede, A. & Ulrichs, K. Highly efficient isolation of porcine islets of Langerhans for xenotransplantation: numbers, purity, yield and in vitro function. *Ann. Transplant.* 6, 48-54 (2001).
15. Herbach, N. et al. Dominant-negative effects of a novel mutated Ins2 allele causes early-onset diabetes and severe beta-cell loss in Munich Ins2C95S mutant mice. *Diabetes* 56, 1268-1276 (2007).
16. Pamir, N. et al. Glucose-dependent insulinotropic polypeptide receptor null mice exhibit compensatory changes in the enteroinsular axis. *Am. J. Physiol Endocrinol. Metab* 284, E931-E939 (2003).
17. Hansotia, T. & Drucker, D. J. GIP and GLP-1 as incretin hormones: lessons from single and double incretin receptor knockout mice. *Regul. Pept.* 128, 125-134 (2005).
18. Hansotia, T. et al. Double incretin receptor knockout (DIRKO) mice reveal an essential role for the enteroinsular axis in transducing the glucoregulatory actions of DPP-IV inhibitors. *Diabetes* 53, 1326-1335 (2004).
19. Preitner, F. et al. Gluco-incretins control insulin secretion at multiple levels as revealed in mice lacking GLP-1 and GIP receptors. *J. Clin. Invest* 113, 635-645 (2004).
20. Gautier, J. F., Fetita, S., Sobngwi, E. & Salaun-Martin, C. Biological actions of the incretins GIP and GLP-1 and therapeutic perspectives in patients with type 2 diabetes. *Diabetes Metab* 31, 233-242 (2005).
21. Gotthardt, M. et al. A new technique for in vivo imaging of specific GLP-1 binding sites: first results in small rodents. *Regul. Pept.* 137, 162-167 (2006).
22. Pfeifer, A., Ikawa, M., Dayn, Y. & Verma, I. M. Transgenesis by lentiviral vectors: lack of gene silencing in mammalian embryonic stem cells and preimplantation embryos. *Proc. Natl. Acad. Sci. U.S.A* 99, 2140-2145 (2002).
23. Klose, R. et al. Expression of biologically active human TRAIL in transgenic pigs. *Transplantation* 80, 222-230 (2005).
24. Moritz, M. W. et al. Chronic central vein catheterization for intraoperative and long-term venous access in swine. *Lab Anim Sci.* 39, 153-155 (1989).
25. Larsen, M. O. et al. Valine pyrrolidide preserves intact glucose-dependent insulinotropic peptide and improves abnormal glucose tolerance in minipigs with reduced beta-cell mass. *Exp. Diabesity. Res.* 4, 93-105 (2003).
26. Kobayashi, K. et al. Development of a porcine model of type 1 diabetes by total pancreatectomy and establishment of a glucose tolerance evaluation method. *Artif. Organs* 28, 1035-1042 (2004).
27. Ricordi, C. et al. Isolation of the elusive pig islet. *Surgery* 107, 688-694 (1990).
28. van der Burg, M. P. & Graham, J. M. Iodixanol density gradient preparation in university of Wisconsin solution for porcine islet purification. *Scientific World Journal.* 3, 1154-1159 (2003).
29. Latif, Z. A., Noel, J. & Alejandro, R. A simple method of staining fresh and cultured islets. *Transplantation* 45, 827-830 (1988).
30. Scherle, W. A simple method for volumetry of organs in quantitative stereology. *Mikroskopie.* 26, 57-60 (1970).
31. Larsen M O, Rolin B, Wilken M, Carr R D, Svendsen O. High-fat high-energy feeding impairs fasting glucose and increases fasting insulin levels in the Göttingen minipig: results from a pilot study. *Ann N Y Acad Sci.* 2002 June; 967:414-23.
32. Liu Y, Wang Z, Yin W, Li Q, Cai M, Zhang C, Xiao J, Hou H, Li H, Zu X. Severe insulin resistance and moderate glomerulosclerosis in a minipig model induced by high-fat/high-sucrose/high-cholesterol diet. *Exp Anim.* 2007 January; 56(1):11-20.
33. S. Schneider: Efforts to develop methods for in vivo evaluation of the native β-cell mass. *Diabetes, Obesity and Metabolism.* December 2008, Vol. 10: 109-118.
34. Ian R. Sweet, Daniel L. Cook, Ake lernmark, Carla J. Greenbaum, Kenneth A. Krohn. Non-invasive imaging of beta cell mass: a quantitative analysis. *Diabetes Technology & Therapeutics.* Oct. 1, 2004, 6(5): 652-659. doi: 10.1089/dia.2004.6.652).

We claim:

1. A transgenic pig whose genome comprises a recombinant nucleic acid encoding a dominant-negative human glucose-dependent insulinotropic polypeptide receptor (GIPR$^{dn}$) operably linked to an insulin promoter that results in expression of the dominant-negative human glucose-dependent insulinotropic polypeptide receptor (GIPR$^{dn}$), wherein said pig expresses the dominant-negative human glucose-dependent insulinotropic polypeptide receptor (GIPR$^{dn}$), and wherein said pig exhibits, as a result of the expression of said receptor, at least one of:
   a) an elevated glucose level following an oral glucose load;
   b) reduced or delayed insulin secretion;
   c) reduced oral glucose tolerance;
   d) reduced pancreatic islet and β-cell mass; and
   e) impaired glucose-dependent insulinotropic polypeptide (GIP) function.

2. The transgenic pig, according to claim 1, wherein the recombinant nucleic acid is a plasmid or viral vector.

3. The transgenic pig, according to claim 2, wherein the recombinant nucleic acid is a lentiviral vector.

4. The transgenic pig, according to claim 3, wherein the recombinant nucleic acid is a lentiviral vector comprising rat insulin 2 gene promoter (RIPII) or pig INS promoter.

5. The transgenic pig, according to claim 1, wherein the recombinant nucleic acid encodes a protein which comprises an amino acid sequence identical to SEQ ID NO:1 except that said amino acid sequence has an amino acid change at residue 332 of SEQ ID NO:1 in the third intracellular loop of the hGIPR, wherein residue 332 of said amino acid sequence is not Ala.

6. The transgenic pig, according to claim 1, wherein the recombinant nucleic acid encodes a protein which has the sequence of SEQ ID NO: 1.

7. The transgenic pig, according to claim 1, wherein the recombinant nucleic acid comprises a sequence having SEQ ID NO: 2.

8. The transgenic pig, according to claim 1, containing the recombinant nucleic acid in its germ cells and somatic cells.

9. The transgenic pig, according to claim 1, wherein hGIPR$^{dn}$ is expressed in the islets of the pancreas.

10. The transgenic pig, according to claim 9, wherein the hGIPR$^{dn}$ is expressed in the β-cells.

11. The transgenic pig, according to claim 1, wherein pancreatic islet and β-cell mass is reduced.

* * * * *

UNITED STATES PATENT AND TRADEMARK OFFICE
CERTIFICATE OF CORRECTION

PATENT NO. : 7,919,673 B2  
APPLICATION NO. : 12/348294  
DATED : April 5, 2011  
INVENTOR(S) : Eckhard Wolf et al.

Page 1 of 1

It is certified that error appears in the above-identified patent and that said Letters Patent is hereby corrected as shown below:

Column 4  
Line 37 "per 105" should read --per $10^5$--

Column 12  
Line 14 "(GIPR dn)" should read --(GIPR$^{dn}$)--

Column 15  
Line 59 "GIPR" should read --GIPR$^{dn}$--

Column 17  
Line 60 "GAG" should read --CAG--

Signed and Sealed this  
Twelfth Day of July, 2011

David J. Kappos  
*Director of the United States Patent and Trademark Office*

SEQUENCE LISTING

<160> NUMBER OF SEQ ID NOS: 4

<210> SEQ ID NO 1
<211> LENGTH: 458
<212> TYPE: PRT
<213> ORGANISM: Artificial Sequence
<220> FEATURE:
<223> OTHER INFORMATION: dominant-negative human glucose-dependent insulinotropic polypeptide receptor (hGIPRdn)

<400> SEQUENCE: 1

```
Met Thr Thr Ser Pro Ile Leu Gln Leu Leu Arg Leu Ser Leu Cys
1               5                   10                  15

Gly Leu Leu Gln Arg Ala Glu Thr Gly Ser Lys Gly Gln Thr Ala
                20                  25                  30

Gly Glu Leu Tyr Gln Arg Trp Glu Arg Tyr Arg Glu Cys Gln Glu
                35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
                100                 105                 110

Arg Asp His Thr Gln Cys Glu Asn Pro Glu Lys Asn Glu Ala Phe Leu
                115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
                180                 185                 190

Leu Leu Pro Arg Pro Gly Pro Tyr Leu Gly Asp Gln Ala Leu Ala Leu
                195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
                260                 265                 270

Pro Trp Val Ile Val Arg Tyr Leu Tyr Glu Asn Thr Gln Cys Trp Glu
                275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Thr Arg
305                 310                 315                 320

Gln Met Arg Cys Arg Asp Tyr Arg Leu Arg Leu Glu Arg Ser Thr Leu
                325                 330                 335

Thr Leu Val Pro Leu Leu Gly Val His Glu Val Val Phe Ala Pro Val
                340                 345                 350
```

```
Thr Glu Glu Gln Ala Arg Gly Ala Leu Arg Phe Ala Lys Leu Gly Phe
        355                 360                 365

Glu Ile Phe Leu Ser Ser Phe Gln Gly Phe Leu Val Ser Val Leu Tyr
    370                 375                 380

Cys Phe Ile Asn Lys Glu Val Gln Ser Glu Ile Arg Arg Gly Trp His
385                 390                 395                 400

His Cys Arg Leu Arg Arg Ser Leu Gly Glu Glu Gln Arg Gln Leu Pro
                405                 410                 415

Glu Arg Ala Phe Arg Ala Leu Pro Ser Gly Ser Gly Pro Gly Glu Val
            420                 425                 430

Pro Thr Ser Arg Gly Leu Ser Ser Gly Thr Leu Pro Gly Pro Gly Asn
        435                 440                 445

Glu Ala Ser Arg Glu Leu Glu Ser Tyr Cys
        450                 455
```

<210> SEQ ID NO 2
<211> LENGTH: 1377
<212> TYPE: DNA
<213> ORGANISM: Artificial Sequence
<220> FEATURE:
<223> OTHER INFORMATION: cDNA sequence of dominant-negative human
      glucose-dependent insulinotropic polypeptide receptor (hGIPRdn)

<400> SEQUENCE: 2

```
atgactacct ctccgatcct gcagctgctg ctgcggctct cactgtgcgg gctgctgctc      60
cagagggcgg agacaggctc taaggggcag acggcggggg agctgtacca gcgctgggaa     120
cggtaccgca gggagtgcca ggagaccttg gcagccgcgg aaccgccttc aggcctcgcc     180
tgtaacgggt ccttcgatat gtacgtctgc tgggactatg ctgcacccaa tgccactgcc     240
cgtgcgtcct gccccctggta cctgccctgg caccaccatg tggctgcagg tttcgtcctc     300
cgccagtgtg gcagtgatgg ccaatgggga ctttggagag accatacaca atgtgagaac     360
ccagagaaga atgaggcctt tctggaccaa aggctcatct tggagcggtt gcaggtcatg     420
tacactgtcg gctactccct gtctctcgcc acactgctgc tagccctgct catcttgagt     480
ttgttcaggc ggctacattg cactagaaac tatatccaca tcaacctgtt cacgtctttc     540
atgctgcgag ctgcggccat tctcagccga gaccgtctgc tacctcgacc tggcccctac     600
cttggggacc aggcccttgc gctgtggaac caggccctcg ctgcctgccg cacggcccag     660
atcgtgaccc agtactgcgt gggtgccaac tacacgtggc tgctggtgga gggcgtctac     720
ctgcacagtc tcctggtgct cgtgggaggc tccgaggagg ccacttccg ctactacctg     780
ctcctcggct ggggggcccc cgcgcttttc gtcattccct gggtgatcgt caggtacctg     840
tacgagaaca cgcagtgctg ggagcgcaac gaagtcaagg ccatttggtg gattatacgg     900
acccccatcc tcatgaccat cttgattaat ttcctcattt ttatccgcat tcttacacgg     960
caaatgcgct gccgggatta ccggctgagg ctcgagcgct ccacgctgac gctggtgccc    1020
ctgctgggtg tccacgaggt ggtgtttgct cccgtgacag aggaacaggc ccggggcgcc    1080
ctgcgcttcg ccaagctcgg cttttgagatc ttcctcagct ccttccaggg cttcctggtc    1140
agcgtcctct actgcttcat caacaaggag gtgcagtcgg agatccgccg tggctggcac    1200
cactgccgcc tgcgccgcag cctgggcgag gagcaacgcc agctcccgga gcgcgccttc    1260
cgggcccctgc cctccggctc cggcccgggc gaggtcccca ccagccgcgg cttgtcctcg    1320
gggaccctcc cagggcctgg gaatgaggcc agccgggagt tggaaagtta ctgctag       1377
```

```
<210> SEQ ID NO 3
<211> LENGTH: 23
<212> TYPE: DNA
<213> ORGANISM: Artificial Sequence
<220> FEATURE:
<223> OTHER INFORMATION: Sense primer

<400> SEQUENCE: 3
tttttatccg cattcttaca cgg                                              23

<210> SEQ ID NO 4
<211> LENGTH: 22
<212> TYPE: DNA
<213> ORGANISM: Artificial Sequence
<220> FEATURE:
<223> OTHER INFORMATION: Antisense primer

<400> SEQUENCE: 4
atcttcctca gctccttcca gg                                               22
```